(12) United States Patent
Rowlen et al.

(10) Patent No.: US 10,948,420 B2
(45) Date of Patent: Mar. 16, 2021

(54) AUTOMATED AGGLUTINATION ANALYZER WITH CONTOUR COMPARISON

(71) Applicant: INDEVR, INC., Boulder, CO (US)

(72) Inventors: Kathy L. Rowlen, Longmont, CO (US); Garrett Wilson, Boulder, CO (US); Gregory Yamada, Boulder, CO (US); Andrew Smolak, Golden, CO (US); Goran Rauker, Boulder, CO (US); Jeffrey T. Ives, Boulder, CO (US)

(73) Assignee: INDEVR, INC., Boulder, CO (US)

( * ) Notice: Subject to any disclaimer, the term of this patent is extended or adjusted under 35 U.S.C. 154(b) by 275 days.

(21) Appl. No.: 16/060,330

(22) PCT Filed: Dec. 9, 2016

(86) PCT No.: PCT/US2016/065950
§ 371 (c)(1),
(2) Date: Jun. 7, 2018

(87) PCT Pub. No.: WO2017/100660
PCT Pub. Date: Jun. 15, 2017

(65) Prior Publication Data
US 2019/0003979 A1 Jan. 3, 2019

Related U.S. Application Data

(60) Provisional application No. 62/265,363, filed on Dec. 9, 2015.

(51) Int. Cl.
*G01N 33/539* (2006.01)
*G01N 33/541* (2006.01)
(Continued)

(52) U.S. Cl.
CPC .......... *G01N 21/82* (2013.01); *G01N 33/539* (2013.01); *G01N 33/541* (2013.01);
(Continued)

(58) Field of Classification Search
CPC ................ G01N 21/82; G01N 33/555; G01N 33/56983; G01N 33/539; G01N 33/541; G01N 2021/825
See application file for complete search history.

(56) References Cited

U.S. PATENT DOCUMENTS 5,389,555 A   2/1995  Watanabe et al.
5,501,838 A   3/1996  Ootani et al.
(Continued)

FOREIGN PATENT DOCUMENTS

EP      0301583 A2       7/1988
WO   WO 2013/175318 A2   11/2013
(Continued)

OTHER PUBLICATIONS

U.S. Appl. No. 15/315,680, filed Jun. 4, 2014.
(Continued)

*Primary Examiner* — Gailene Gabel
(74) *Attorney, Agent, or Firm* — Leydig, Voit & Mayer, Ltd.

(57) ABSTRACT

The systems and methods contained herein are directed toward automated analysis of agglutination reactions to determine properties of materials, including viruses and vaccines thereto. Advanced digital imaging and processing techniques are used to determine the presence or absence of viruses or antibodies within a fluid sample. The systems and methods are versatile, and can be used to determine specific properties of biomaterials and viruses, such as titer value, concentration, genotype, phenotype, serotype, vaccine efficacy, viral resistance and other properties of relevance in the
(Continued)

medical, research and development fields. Also provided are systems and methods of standardization, repeatability, and data storage and transmittal to reduce errors and subjectivity inherent to conventional assays characterized by human readers.

27 Claims, 12 Drawing Sheets

(51) Int. Cl.
G01N 33/555 (2006.01)
G01N 21/82 (2006.01)
G01N 33/569 (2006.01)
G06T 7/12 (2017.01)
G06T 7/10 (2017.01)
G06T 7/90 (2017.01)

(52) U.S. Cl.
CPC ..... *G01N 33/555* (2013.01); *G01N 33/56983* (2013.01); *G01N 2021/825* (2013.01); *G06T 7/10* (2017.01); *G06T 7/12* (2017.01); *G06T 7/90* (2017.01); *G06T 2207/20116* (2013.01)

(56) References Cited

U.S. PATENT DOCUMENTS

| | | | |
|---|---|---|---|
| 5,578,269 | A | 11/1996 | Yaremko et al. |
| 6,051,191 | A | 4/2000 | Ireland |
| 8,962,256 | B2 | 2/2015 | Kachurin et al. |
| 9,360,433 | B1 | 6/2016 | Rowlen et al. |
| 2004/0246483 | A1 | 12/2004 | Hansen et al. |
| 2005/0112607 | A1 | 5/2005 | Bamdad et al. |
| 2009/0253218 | A1 | 10/2009 | Wardlaw et al. |
| 2009/0287419 | A1 | 11/2009 | Haga |
| 2009/0325148 | A1 | 12/2009 | Kachurin et al. |
| 2014/0045170 | A1* | 2/2014 | Patel ............. G01N 33/86 435/5 |
| 2014/0356969 | A1 | 12/2014 | Nishikawa et al. |
| 2015/0152489 | A1 | 6/2015 | Castro Signoret et al. |
| 2019/0293665 | A1* | 9/2019 | Patel ............. G01N 33/6854 |

FOREIGN PATENT DOCUMENTS

WO  WO 2014/015194 A2  1/2014
WO  WO 2017/100652 A1  6/2017

OTHER PUBLICATIONS

U.S. Appl. No. 13/494,802, filed Jun. 12, 2012.
U.S. Appl. No. 15/740,756, filed Jun. 30, 2016.
U.S. Appl. No. 15/740,761, filed Jun. 30, 2016.
Aubert et al. (Jun. 12, 1995) "Automated reading and processing of quantitative IgG, IgM, IgA and IgE isotypic agglutination results in microplates Development and application in parasitology-mycology'" J. Imm. Methods 186:323-328.
International Preliminary Report on Patentability dated Jun. 21, 2018 in PCT/US2016/065940.
International Preliminary Report on Patentability dated Jun. 21, 2018 in PCT/US2016/065950.
International Search Report and Written Opinion dated Apr. 13, 2017 in PCT/US2016/065940.
International Search Report and Written Opinion dated Feb. 23, 2017 in PCT/US2016/065950.

* cited by examiner

Fixed QC Plate

Actual HA Assay

AUTOMATED AGGLUTINATION ANALYZER WITH CONTOUR COMPARISON

CROSS REFERENCE TO RELATED APPLICATIONS

This application is a U.S. National Stage Application under 35 U.S.C. § 371 of International Application No. PCT/US2016/065950, filed Dec. 9, 2016, which claims the benefit of priority to U.S. Provisional Patent Application No. 62/265,363 filed on Dec. 9, 2015, each of which is specifically incorporated by reference to the extent not inconsistent herewith.

STATEMENT REGARDING FEDERALLY SPONSORED RESEARCH OR DEVELOPMENT

This invention was made with government support under Grand number R44AI106054 by the National Institute of Health (NIH). The government has certain rights in the invention.

BACKGROUND

Agglutination reactions play an important role in medical diagnostics as well as vaccine research and synthesis. For example, the presence or absence of agglutination can be used to determine the presence of either viruses or virus antibodies in a wide range of materials including blood, urine, saliva, cerebrospinal fluid, respiratory tract fluids, cell cultures, or egg cultures. Further, by diluting analytes over a range of concentrations, agglutination reactions can be used in a wide range of common medical practices including blood typing, diagnosis of viruses such as influenza or autoimmune disorders such as rheumatoid arthritis, determination of viral titer or concentration and viral and bacterial serotyping.

Agglutination refers to the process in which surface binding between cells or other functionalized small particles (such as latex beads) and an antibody or complement causes the clumping of cells or particles to form larger complexes or interconnected networks of particles. These complexes become much more prone to remain suspended within a solution, and thus agglutination can be optically or visually detected by observing a solution of cells or particles. Cells or particles which are not agglutinated, referred herein as non-agglutinated, settle under the force of gravity to the bottom of a vessel, with the settled cells visually observable as a dark region or button on the bottom. Agglutination reactions are typically performed in 96 well plates of various dilutions. After the solutions are prepared, they are allowed to rest and non-agglutinated cells or particles drift to the bottom and become visible, forming the optically opaque button in the bottom of the vessel. In wells in which agglutination has taken place, the complexes remain suspended throughout the solution and the well liquid retains a uniform color without any optically observable button associated with the settled, non-agglutinated cells or particles. Then, based on the amount of dilution in the various wells combined with which wells agglutinated and which did not, a virus or antibody titer may be established. This process is complicated by the fact that the transition between agglutinated and non-agglutination often has a transitional appearance, where two to four dilutions in a series show a partial but incomplete degree of agglutination. Further, non-specific inhibition can occur where some other agent within the sample causes a less pronounced, but still noticeable agglutination reaction.

Unfortunately, because agglutination may be used with many different cell types, lines, particle types, and binding antibodies or agents, each type of reaction may have a different appearance making automation of determining whether or not agglutination has occurred difficult. Humans can easily differentiate between opaque buttons and transparent solutions and, accordingly, conventional practice is to use human expert readers to personally analyze each 96 well plate within 30 minutes of mixing of the reagents in order to determine if agglutination has occurred, and often, to determine a titer value. After 30 minutes, an agglutinated complex may also begin to settle and a new assay prepared to avoid erroneous readings. Due to differences in technique as well as inherent vulnerability arising from human subjectivity, titer values often differ between different laboratories or even different readers working in the same laboratory. The variance is pervasive to the point that titer values within one titer call or dilution factor of each other are still characterized as a correct reading. Thus, for a consensus titer value of 128 in a two-fold dilution series, a determination of a titer value of either 64 or 256 would be considered acceptably accurate.

Prior attempts have been made to automate the determination of agglutination and establishing titer values, but with limited success. For example, it has been established that laser light or other light may be focused through a well and agglutination determined based on the amount of light transmitted (Aubert et al., "Automated reading and processing of quantitative IgG, IgM, IgA, and IgE isotypic agglutination results in microplates: Development and application in parasitology). Additionally, digital imaging has previously been suggested as a means for determining agglutination. For example, U.S. Pat. No. 8,962,256 to Kachurin et al. teaches the use of digital imaging, in conjunction with activated wells in which reactions occur on the well surface, to establish a measure of degree of agglutination based on ratio of the size of agglutination patterns and intensity within the agglutination pattern. The ratio is then correlated graphically to the ratio for a calibration curve to calculate concentration of an unknown. However, those methods fail to achieve reliable repeatability.

Accordingly, there remains a need in the art for systems and methods capable of detecting agglutination and establishing titer values which are automated, reduce or eliminate the need for expert human readers, provide greater standardization between different operators and laboratories and reliably detect agglutination or non-agglutination as well as non-specific inhibition and errors which may otherwise tarnish results.

SUMMARY

The systems and methods provided herein are directed toward the automated analysis of agglutination reactions to determine the presence or properties of materials such as from biomaterials or particles, including viruses. In particular, advanced digital imaging and processing techniques are used in agglutination assays or in agglutination inhibition assays, including, for example, to determine the presence or absence of viruses or antibodies. The systems and methods provided herein are robust and versatile, and can be used to determine specific properties of a material, such as viruses, including titer value, concentration, genotype, phenotype, serotype, vaccine efficacy, viral resistance and other properties important to medical professionals. The systems and methods provide various functional benefits, including standardization, repeatability, and the ability for data storage and transmittal, thereby reducing errors and subjectivity inherent to human readers, all while improving efficiency and decreasing costs. The systems and methods are particularly versatile in identifying and characterizing vessels that otherwise do not squarely fall into an agglutination or non-agglutination condition, such as vessels having a non-specific type of binding event that impacts agglutination characteristics.

The systems and methods provided herein automatically segment an image of a plate containing multiple wells into several images corresponding only to areas in which agglutination could occur, namely the reaction vessel. The images are then analyzed individually for agglutination using a contour comparison process wherein each well is compared to a control well. Advantageously, the contour comparison process is capable of differentiating between agglutinated, non-agglutinated, non-specific inhibition or an error state within the control well. Further, the introduction of a quality control plate allows for the comparison of settings and parameters being used by different laboratories as well as a verification that the systems and methods are working properly.

In an aspect, provided are methods for determining an agglutination parameter with particles in a fluid sample, the method comprising the steps of: (i) providing a reaction plate having a plurality of reaction vessels for receiving the fluid sample; (ii) introducing an agglutinating mediator to at least a portion of the plurality of reaction vessels, wherein the introduced agglutinating mediator in the reaction vessels spans a dilution range over the at least a portion of the plurality of reaction vessels; (iii) introducing a particle solution to each of the plurality of reaction vessels; (iv) creating a digital image of the plurality of reaction vessels; (v) processing the digital image to generate a processed image, wherein the step of processing comprises defining a plurality of areas of the processed image corresponding to each of the plurality of reaction vessels and each of the areas correspond to a plurality of pixels; (vi) measuring within each of the defined plurality of areas a pixel intensity for each of the plurality of pixels positioned within the area; (vii) identifying a boundary contour, if present, for each of the reaction vessels from the measuring step; (viii) calculating a one or more boundary contour parameters for each of the identified boundary contours; (ix) comparing each of the calculated one or more boundary contour parameters in each of the reaction vessels with a one or more standard boundary contour parameters to determine an agglutination condition in each of the plurality of reaction vessels, wherein the agglutination condition is one of: agglutination, non-agglutination, non-specific inhibition, or error state; and (x) determining the agglutination parameter from the agglutination condition in each of the plurality of reaction vessels over the dilution range. The number labelling the steps provided are for reference only and the order in which the steps of the provided method are performed may be, in some cases, performed in a different order than listed. For example, the particle solution may be introduced to the reaction vessels prior to the agglutination mediator, or vice versa. In an aspect, the last component added to make the fluid sample is the particle solution.

The agglutination parameter may be any relevant parameter associated with agglutination and/or agglutination inhibition. For example, agglutination parameter may be one or more of a titer value, concentration, genotype, phenotype, serotype, viral resistance, inhibition, presence of the agglutinating mediator; and absence of the agglutinating mediator. The particles may be any particle that is capable of settling in a solution under non-agglutination conditions but, in contrast, do not readily settle when undergoing agglutination, as mediated by an agglutination mediator. In an aspect, the particle has biological components, such as one or more of: red blood cells, white blood cells, tissue cells, bacteria. The methods and systems are also compatible with non-biological particles or a combination of artificial and natural components, including synthetic particles including protein-coated metal, polymer objects, and/or carbon-embedded cholesterol objects. The agglutinating mediator may be one or more of: a virus, an antibody, antibody fragment, a complement, a protein, a lectin, a vaccine, a vaccine component, or a combination thereof. In an embodiment, for example, the method is a hemagglutination assay or, alternatively, a hemagglutination inhibition assay. For example, an agglutinating mediator that is a virus and a vaccine or vaccine component thereto may be used in an agglutination inhibition assay, such as to check vaccine titer.

In an embodiment, for example, the one or more standard boundary contour parameters is a user-provided value. In an embodiment, any of the systems and methods further comprise the steps of: (i) introducing a control fluid sample into the control reaction vessel, wherein the control fluid sample non-agglutinates and forms a central button in a central region of the control reaction vessel; (ii) creating a digital image of the control reaction vessel; (iii) processing the digital image to generate a processed image, wherein the step of processing comprises defining a control area of the processed image corresponding to the control reaction vessel and the control area corresponds to a plurality of pixels; (iv) measuring within the defined control area a pixel intensity for each of the plurality of pixels positioned within the area; and (v) identifying a standard non-agglutination boundary contour with a one or more standard boundary contour parameter for the control fluid sample in the control reaction vessel, from the measuring step. Further, reaction vessels may be arranged in an array and the control reaction vessel is a one or more control reaction vessel positioned in the array at one or more of: one or more rows of the array or one or more columns of the array allowing one or more control reaction vessels to be distributed in either rows or columns within the array. Accordingly, a user-provided value may itself be generated from one or more control reaction vessels in the plate, or from a previously provided plate so that the control reaction may be run on an initial plate, but not subsequent plates, thereby saving time and effort.

The systems and methods automate the process of capturing an image of multiple agglutination reactions and separating areas within the image to generate an individual image that corresponds to each individual well within the reaction plate. Further, the reaction vessels of the reaction plates may be optically isolated during image capture to reduce noise and increase accuracy of analyzing the image for agglutination. This provides more accurate and comprehensive analysis of the individual images corresponding to each well and eliminates areas of the image which provide no value to the analysis and, in fact, may increase noise, decrease reliability and sensitivity, therefore, adversely impact device performance.

The control reaction vessel in any of the provided systems and methods may comprise at least two control reaction vessels wherein: (i) a first control reaction vessel is a positive control reaction vessel where agglutination occurs so that no button is optically detected; and (ii) a second control reaction vessel is a negative control reaction vessel where non-agglutination occurs and a centrally-positioned button is optically detected. Further, one or more standard boundary contour parameter's user-provided value may be from a reaction plate having the control reaction vessel used in a prior method.

In an embodiment, for example identifying the boundary contour step comprises edge detection, for example, edge detection comprising identifying a pixel intensity gradient that is greater than or equal to a reference or user-selected pixel intensity gradient. The reference pixel intensity gradient may be from a control reaction vessel. In embodiments, the boundary contour parameters are one or more of: (i) an area defined by the boundary contour; (ii) a perimeter of the boundary contour; (iii) a circularity of the boundary contour, for example a ratio of the minor and major radii; (iv) an optical intensity of a region within the boundary contour; (v) an average pixel gradient intensity of the boundary contour; (vi) a ratio of average pixel intensity of a region within the boundary contour to average pixel intensity in a region outside the boundary contour; (vii) a location of the boundary contour within the area of the image corresponding to the reaction vessel; (viii) one or more diameters of an area defined by the boundary contour; and (ix) a pixel intensity density within the reaction vessel. Non-specific inhibition may be identified in a reaction vessel having a non-uniform boundary contour or multiple boundary contours. Further, an error may be from a control reaction vessel without an identifiable boundary contour.

In any of the systems and methods provided, the boundary contour parameters may be one or more of area of a region defined by said boundary contour, circularity, or location of said boundary contour within the reaction vessel. In an embodiment, any of the systems and methods may further comprise a step of automatically optically detecting a position of said control reaction vessel.

In an embodiment, for example, any of the methods provided herein may further comprise the step of positioning the reaction plate in a receiver plate, wherein the receiver plate has a plurality of openings aligned with the plurality of reaction vessels to optically isolate the areas corresponding to the plurality of reaction vessels. This can increase an optical contrast between a well boundary of each of the reaction vessels and a fluid sample receiving volume formed by the well boundary. In an embodiment, the step of processing the digital image further comprises isolating a red channel of the captured digital image to further improve locating the area of the processed image corresponding to each of the reaction vessels. The red light channel may correspond to light having a wavelength greater than or equal to 600 nm and less than or equal to 800 nm.

Provided herein are methods and systems of autonomously analyzing images of reaction wells to determine whether or not an agglutination condition has occurred in the corresponding reaction well. The systems and methods provided herein are capable of accurate analysis and may be adjusted in a number of ways to ensure the results obtained from the automated optical detection and calculation correspond and align with the results which would have been obtained by a human expert reader. The methods and systems utilize advanced image processing techniques and user adjustability to ensure accurate agglutination determination and calculation of agglutination parameters, such as titer.

In an embodiment, the step of processing the digital image further comprises converting the digital image to a greyscale image or, for example, dilating and eroding the digital image by applying a rectangular structural element. In an embodiment, the step of processing the digital image further comprises performing a Gaussian blur of the digital image. In embodiments, for example, the step of processing the digital image further comprises separating the digital image into a red channel, a blue channel and a green channel.

Advantageously, the systems and methods also standardize agglutination reaction analysis between different laboratories and users and also as a check of instrument and algorithm fidelity. A quality control plate may be utilized to verify that the systems and methods contained herein are appropriately analyzing simulated agglutination conditions.

In embodiments, for example, the methods provided further comprise the steps of: (i) providing a quality control plate and repeating the creating, processing, measuring, identifying, calculating, comparing and determining on the quality control plate; and (ii) comparing the determined agglutination parameter for the quality control plate against an expected agglutination parameter for the quality control plate; thereby obtaining an instrument verification parameter from the quality control plate. In an embodiment, the quality control plate comprises a plurality of vessels with optically dense buttons and a plurality of vessels without optically dense buttons and the method further comprises standardizing the method across different automated agglutination analyzers that implement the method. In an embodiment, the quality control plate contains no liquid. In an embodiment, the quality control plate is a 96-well plate and the quality control plate reaction vessels are filled with a colored polymer and at least one reaction vessel has an optically dense button corresponding to a solid, centrally-positioned within the reaction vessel and embedded in the polymer.

The systems and methods provided herein are versatile and may be used to determine properties of cells or particles from a wide range of sources. Additionally, results from image analysis may be saved indefinitely so that they may later be reviewed or checked for errors. In an embodiment, the dilution range is generated by diluting a sample by a factor greater than or equal to 1:1 and less than or equal to 16384:1.

In embodiments, the agglutinating mediator is from blood, urine, saliva, cerebrospinal fluid, respiratory tract fluids, a cell culture, an egg culture, or may be a vaccine formulation. In an embodiment, for example, the system and methods are used to measure titer of influenza virus or anti-influenza virus antibodies. In an embodiment, any of the images and associated boundary contour parameters are saved for subsequent further analysis or quality control assessment. In embodiments, the systems and methods are operated in batch mode followed at a later time by a user-approved titer call for selected reaction plates.

Also provided herein are agglutination analyzers for carrying out any of the methods provided herein. In an embodiment, the analyzer is an automated agglutination analyzer comprising: (i) a receiver plate having a top surface and a plurality of openings extending through the top surface; (ii) a reaction plate having a plurality of reaction vessels, wherein the reaction plate is positioned on the top surface of the receiver plate with the plurality of reaction vessels optically and physically aligned with the plurality of openings; (iii) an optical source in optical communication with the reaction plate; (iv) an optical detector to detect light from the optical source and that passes through the plurality of reaction vessels and the plurality of openings; (v) a processor to process a digital image obtained by the optical detector; and (vi) a display to display an agglutination parameter for the reaction plate during use.

In an embodiment, the analyzer further comprises a quality control plate for analyzer status validation, for example, a quality control plate comprising: a colored polymer having a color that substantially matches a fluid color of the fluid sample; in a first subset of reaction vessels, a solid element embedded in the polymer and centrally positioned within the reaction vessel to correspond to a non-agglutination condition; and in a second subset of reaction vessels, no solid element embedded in the polymer to correspond to an agglutination condition.

In an aspect, provided are methods for determining a validation status of an automated agglutination analyzer, the method comprising the steps of: (i) providing a quality control plate to a reservoir plate of the analyzer, wherein the quality control plate has a plurality of wells, including a first set of wells having an optically dense button and a second set of wells without the optically dense button; (ii) creating a digital image of the plurality of wells; (iii) processing the digital image to generate a processed image, wherein the step of processing comprises defining a plurality of areas of the processed image corresponding to each of the plurality of wells; (iv) measuring within each of the defined plurality of areas a pixel intensity for each of the plurality of pixels positioned within the area; (v) identifying a boundary contour, if present, for each of the plurality of wells from the measuring step; (vi) calculating a one or more boundary contour parameters for each of the identified boundary contours; and (vii) comparing each of the calculated one or more boundary contour parameters in each of the reaction vessels with a one or more standard boundary contour parameters, thereby determining validation status of the automated agglutination analyzer.

DETAILED DESCRIPTION

Figure 1:
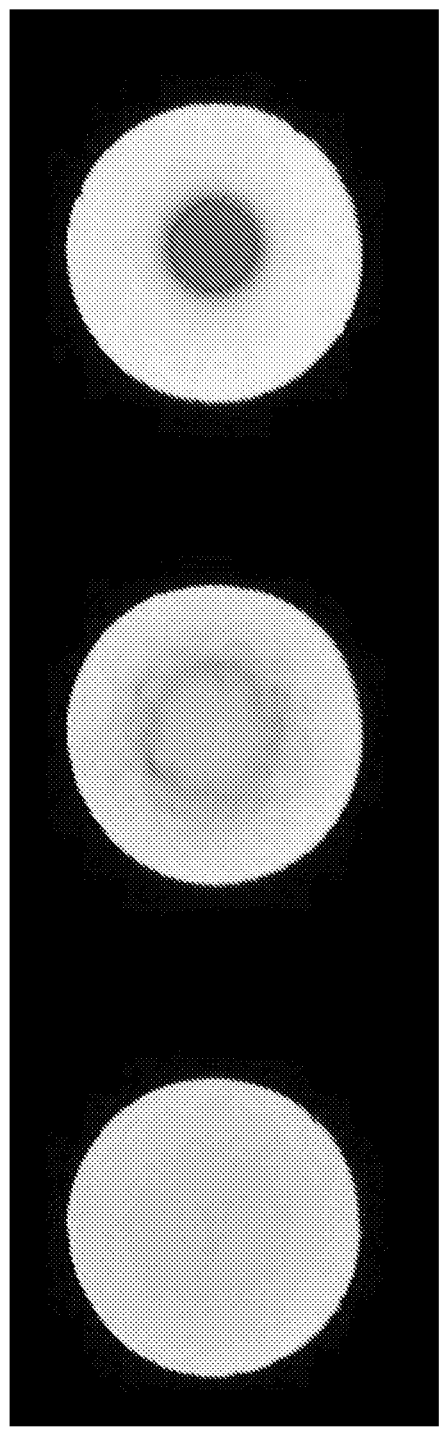
FIG. 1 is an illustration of a fully agglutinated reaction vessel, a transitional reaction vessel, and a non-agglutinated reaction vessel.

In general the terms and phrases used herein have their art-recognized meaning, which can be found by reference to standard texts, journal references and contexts known to those skilled in the art. The following definitions are provided to clarify their specific use in the context of the invention.

"Agglutination parameter" refers to a property of a component of a fluid sample that can be determined and/or inferred from the presence or absence of agglutination within the sample under various conditions. The agglutination parameter may refer to the presence or absence of an agglutination mediator of interest in the fluid sample, for example, whether a sample contains a virus. Agglutination parameter may be a property or presence of the particle solution and/or a property or presence of an agglutinating mediator in the fluid sample. In an embodiment, agglutination parameter refers to the presence, absence, titer or concentration of the agglutinating mediator, such as a virus or antigen. In an embodiment, the agglutination parameter refers to the efficacy of an agglutinating mediator, such as an antibody, serum component, vaccine, or vaccine component, in preventing the binding or reacting of a second agglutinating mediator, for example, a virus or antigen. In embodiments, agglutination parameter may reference a property of the particle solution such as genotype, phenotype, or serotype, subtype.

"Agglutination condition" refers to the physical condition of particles and mediators within a reaction vessel. In an embodiment, for example, agglutination condition refers to a condition of agglutinated, non-agglutinated, non-specific inhibition, or error state. In an embodiment, agglutination condition refers to a binary state in which the well is either agglutinated or non-agglutinated.

"Fluid sample" refers to a volume of fluid contained in each well. A fluid sample may be a sample of biological material taken from an organism, a synthetic molecule or solution or a combination thereof. In an embodiment, fluid sample refers to a combination of a particle solution and one or more agglutination mediators. In another embodiment, fluid sample refers to a mixture of red blood cells in solution, a virus and, optionally, an antibody, vaccine, or serum.

"Particle solution" refers to a plurality of particles in a fluid capable of binding with an agglutination mediator to form agglutination complexes. In an embodiment, the particles within the particle solution are red blood cells, for example, human, bovine, porcine, avian, ovine, canine, or other red blood cells. In another embodiment, the particles may be white blood cells, tissue cells, bacteria, synthetic particles including protein-coated metal and polymer objects, or carbon-embedded cholesterol objects. The solution in which the particles are obtained may be associated with the particles, such as plasma for blood cells, it may be a specifically prepared solution to induce or promote agglutination, or any other liquid medium, such as water or a solvent that is compatible with the particles, including in combination with appropriate buffers to maintain the desired functionality of particles.

"Agglutination mediator" is used broadly herein to refer to substances that are capable of binding with other particles to either promote or inhibit the formation of agglutination complexes. Agglutination mediator, therefore, may refer to a single type of binding substance or it may refer to a mixture of multiple binding substances, which may or may not be in competition for binding sites in the formation of agglutination complexes. For example, agglutination mediator may refer to a virus, or alternatively, it may refer to both a virus and an antibody in competition for similar binding sites upon particles, such as red blood cells. This reflects that the methods and systems provided herein are equally applicable for agglutination assays or agglutination inhibition assays, for example, hemagglutination (HA) or hemagglutination inhibition (HI) assays.

"Pixel" refers to a point in a digital image, such as a single scalar element of a multi-component image. In an embodiment, it refers to a single cell in a rectangular grid of points of color that combine to form a visible image. In an embodiment, pixels are a combination of multiple light intensities corresponding to different colored light channels. In an embodiment, pixels are a combination of red, green and blue light intensities. In an embodiment, for example, pixels may be a single point of a digital image corresponding to an intensity of a single channel of light. The total number of pixels, therefore, will change depending on a number of factors, such as optical detector resolution and magnification.

"Threshold intensity" refers to an arbitrary value of light intensity in which an individual pixel is separated into two different categories or states; low or high-intensity state. For example, threshold intensity may be used to define a pixel as either low-intensity or black, or high-intensity or white in a greyscale image, wherein all pixels thereafter defined as either wholly black or wholly white. In an embodiment, threshold intensity may be adjusted by a user or operator.

"Boundary contour" or "boundary edge" are used interchangeably and refer to a transition boundary between one or more different visible areas within a digital image, for example, the transition between a transparent/translucent area of an image to a relatively opaque area. Boundary contours may also be defined as a transition between an area of high-intensity pixels to an area of low-intensity pixels. In an embodiment, for example, a boundary contour refers to the boundary represented in a digital image between the settled particles, such as red blood cells, i.e. the button and the periphery of remaining sample fluid in a non-agglutinated reaction.

"Boundary contour parameter" refers to a parameter which may be determined based on a boundary contour. For example, a boundary contour parameter may be an area inside or outside a boundary contour, a perimeter of a boundary contour, the circularity of a boundary contour, the location of a boundary contour relative to the edge of the reaction vessel or the center of the reaction vessel, a calculated origin or central position of the region defined by the boundary contour within the well, a diameter or radius, the signal amplitude of pixels inside and/or outside a boundary contour, as well as averages and associated statistical characterizations thereof, such as a standard deviation. A boundary contour parameter provides information regarding the physical characteristic of a boundary contour and, more specifically, information about the region defined by the boundary contour. Examples include non-agglutinated regions within a captured digital image. For example, the boundary contour parameters may be used to numerically describe the size, shape, and/or location of an agglutination region or "button" (including both specific and non-specific agglutination due to non-specific inhibition).

Similarly, a "standard boundary contour parameter" refers to a parameter that is provided, directly or indirectly, from a control reaction vessel. The control may be a part of the reaction plate itself that is being assayed, or from a reaction plate that was previously assayed and that is used to provide control parameters for subsequent assays.

"Control reaction vessel" refers to an agglutination reaction vessel which provides controlled, known conditions to reliably provide agglutination or non-agglutination conditions. For example, in a negative or non-agglutination control, no pro-agglutination mediator is added or any pro-agglutination mediator is overwhelmed by any an anti-agglutination mediator, so that the vessel represents a well without any interaction between the particle solution and the agglutination mediator. Alternatively, a positive control reaction vessel is one in which a known quantity of agglutination mediator is added to facilitate an agglutination condition.

"Edge detection" refers to an algorithm that determines a boundary contour or boundary edge based on adjacent areas. Edge detection is a digital imaging technique wherein software analyzes a selected group of pixels, or a kernel, and compares the intensity of the kernel to the intensity of surrounding pixels to determine if the intensities are changing in a way that suggests an edge or a boundary contour exists. In an embodiment, edge detection measures the intensity gradient between the kernel and the surrounding pixels or kernels to define a boundary contour, with a boundary contour identified for intensity or signal intensity gradients that exceeds a user-defined intensity or intensity gradient.

"Vessel" or "well" are used interchangeably and refer to an area on a plate bottom or a volume extending therefrom designed to hold and contain a fluid. Vessels and wells may be physically enclosed on all sides, or open on one plane to allow introduction of additional fluids. In an embodiment, vessel or well refers to an individual U or V shaped chamber within a reaction plate or an ELISA plate, including a 96-well plate or 384-well plate to facilitate dilution and titer determinations arising from a serial dilution.

"Receiver plate" refers to a device designed to physically accept and hold a reaction plate. In an embodiment, the receiver plate optically separates individual wells within a reaction plate and reduces light scatter between the wells. In an embodiment, a receiver plate physically locates each well so that the individual well is repeatedly positioned in the same physical location with respect to a digital imaging device or an optical source.

"Quality control plate" refers to a fabricated reaction vessel designed to closely mimic the optical properties of a typical agglutination assays. In an embodiment, the quality control plat simulates color and optical density of various agglutination reaction results. The quality control plate, when imaged, creates a similar image to that of a typical agglutination assay. The individual wells within the quality control plate may simulate an agglutinated state, a non-agglutinated state, a non-specific inhibition. In an embodiment, the quality control plate is solid, to remove the possibility of spilling or contaminating the contents of the wells. In an embodiment, the quality control plate is stable at ambient temperatures, stable for periods of time greater than one year, or both.

"Instrument verification parameter" refers to a numerical or empirical indication that an agglutination analyzer is operating within acceptable limits and providing accurate results. In embodiments, an instrument verification parameter may accurately identify simulated optically dense buttons in a quality control plate. In an embodiment, the instrument verification parameter may refer to an adjustable value, such as threshold intensity or threshold pixel count associated with the device in question as to be compared with similar data for other devices. Such a parameter is a useful indication that a device is operating properly and in accordance with manufacturer specification. An instrument verification parameter may, therefore, correspond to pass/fail, where a fail indicates additional follow-up should be performed prior to any additional assaying.

"Optical source" refers to a light source that illuminates the reaction plate and is used to ensure a desired digital image is obtained, such as by using an optical detector. The optical source may be in line of sight with the detector or may utilize reflective optics to ensure the optical source is in optical communication with the well, the detector or both.

"Optical detector" refers to a device that may be used to obtain a digital image, for example, a CCD, CMOS device, a digital camera, or a high resolution digital camera.

"Optical communication" refers to components that optically communicate with each other, in a manner that preserves each component's desired functionality. For example, a receiver and reaction plate are in optical communication with each other in that the relevant areas of the plate are imaged, with the physical contact between the components that provides a desired positioning without adversely impacting light transmission through each and every reaction well.

"Validation status" refers to a status in which the device is accurately identifying agglutinated reaction vessels or simulated agglutination like reaction vessels within a quality control plate.

Expert human readers remain the dominant method for analyzing agglutination assays and rely on a person experienced with characterizing the assays to visually determine a difference between the agglutinated and non-agglutinated state. The visual appearance of the agglutinated and non-agglutinated states depend on several factors, such as the container, the type of particle in solution (red blood cells, latex microspheres, etc.), and the concentration of particles and "bridging" components, such as the agglutination mediators. The change from non-agglutinated to agglutinated occurs when the "bridging" components such as a virus, antibody, bacterium, or other material bind to the particles in solution and create a relatively large network or lattice or function to block this agglutination. Such an agglutinated network generally fixes the positions of the particles, significantly reducing any mobility, such that settling due to gravity is retarded.

For example, the appearance of influenza HA and HI assays are the result of agglutination assays involving red blood cells, influenza virus, and anti-influenza antibodies performed in multi-well plates, such as 96-well plates with U or V bottom shaped wells. A non-agglutinated reaction appears as an optically dense spot in the center of the well because the non-agglutinated red blood cells sink to the bottom of the well, and is positioned in the center due to the bottom curvature, such as a U or V shaped bottom curvature, with the low point centered in the middle of the well. In contrast, the agglutinated state appears as a diffuse red color across the entire well as the binding between the red blood cells and influenza virus forms a diffuse, suspended lattice. The visual appearance of the wells in these two ideal states is ideally readily apparent—clear periphery with dark central spot (non-agglutinated) versus diffuse red color across the entire well (agglutinated). The specific appearance varies with the type of plate (U vs V), red blood cell type (guinea pig, avian, horse, etc.), and blood cell concentration, but the overall distinction is always between diffuse agglutination and non-agglutinated spot, or button. Expert readers adjust to each varied condition. Of course, for particles that are not RBCs, the color of the diffuse agglutination and non-agglutinated spot may be different.

The goal of many agglutination assays, like influenza hemagglutination and hemagglutination inhibition, is to determine the relative effect of different viruses (or antibody or other bridging-related component) on many samples. The appearance of agglutination depends on the concentration and avidity of the virus, so agglutination assays often involve a dilution series of the virus (also referred herein as a bridging agent or an agglutination mediator). The transition point between agglutinated and non-agglutinated appearance is referred to as the titer of the virus, and is usually presented as the dilution factor for that particular well. For example, if the virus or antibody is diluted by a factor of 32 in the transition well, then the HA or HI titer is 32.

In practice, the primary challenge for the human or automated reader is not resolving the clear cases of agglutinated versus non-agglutinated, but distinguishing the transition point across wells with mixed proportions of agglutinated and non-agglutinated material that may result in a vaguely observable or disfigured button. For hemagglutination assays, this involves distinguishing wells that appear to have varying degrees of both buttons and uniform coloration.

Hemagglutination assays typically analyze 8 different virus samples by creating a dilution series of virus across each row of a 96 well plate (8 rows by 12 columns.) The last column in the plate often has no virus to create a non-agglutinated "control" well for each sample/row. Alternatively, HA assays can also be set up creating the dilution series down each column of a plate, with the last row in the plate acting as a control well. A constant volume and concentration of red blood cells are added to each well, and after an appropriate incubation period, the wells are visually examined for agglutination. Most of the wells for a given sample are clearly agglutinated or not. But, the transition from agglutinated to non-agglutinated usually occurs across 2 to 4 wells that will have indications of both buttons and uniform color. The difference in appearance of two adjacent wells is not dramatic, but the reader is expected to select a single well (and therefore a titer value.) The same challenge of interpreting the transition point occurs with hemagglutination-inhibition assays and other agglutination assays, although the reagents added to the plate are different. In HI, the titer of antibody that binds to the virus may be determined, for example. FIG. 1 illustrates fully- and non-agglutinated reaction vessels (left-most and right-most images, respectively), as well as a more difficult transitional reaction (middle image).

Human readers will often use a technique of physically tilting hemagglutination assay plates to look for movement of the "button" as an additional guide to aid titer interpretation. The angle, rate of movement, and exact visual characteristics distinguishing agglutinated from non-agglutinated wells during tilting vary between different individuals and laboratories. The tilting and flattening of the plate may be repeated several times as the operator evaluates different wells and confirms their readings. In some laboratories, more than one reader is used to confirm titer decisions made by the first reader.

Occasionally, the transition between agglutinated and non-agglutinated never occurs for the chosen dilutions, and titers are assigned as ">the maximum dilution factor" or "<the minimum dilution factor" depending on the appearance. For example, a row in a HA assay where all the wells show agglutination and a maximum dilution factor of 2048 and would be assigned a titer value of ">2048." Conversely, a row in an HA assay with a minimum dilution factor of 8 and all the wells appear non-agglutinated would be assigned a value of "<8." In some cases, the transition point may be the first or last well (minimum or maximum dilution), but resolving whether that well is the transition point can lead to different readers assigning the last well and others assigning the <or> value.

The difficulty of precisely identifying the transition or titer well is the primary reason that most laboratories have specific, experienced personnel serving as expert readers. Even with the use of well-trained experts, titer assignments across different readers and laboratories are not identical and are generally considered accurate if they are within 1 well of the "correct" value. For example, if the consensus titer value was 128, then either 64 or 256 would be considered acceptable in a typical two-fold dilution series.

In addition to visually reading correct titers, laboratories using agglutination assays must accurately track and record each sample's titer value and the associated testing conditions. Some laboratories process thousands of samples and hundreds of plates per day, creating a complex system of manual reading and recording, followed by transcription into electronic records. The likelihood of errors is relatively high, and the cost of personnel to manage and reliably perform the varied tasks is significant.

Agglutination assays are performed worldwide, with the use of HI assays an example of a critical case. Influenza vaccine manufacturers look to the World Health Organization (WHO) and its system of international laboratories for guidance on the specific strains and subtypes of circulating influenza. One aspect of this program involves hemagglutination inhibition assays to identify which vaccine components are most effective at eliciting an immune response. Vaccine components typically being hemagglutinin or neuraminidase proteins or protein fragments that often elicit an immune response in the infected individual. Multiple laboratories processing hundreds of samples each measure the antibody titer associated with the potential vaccine components. Based on the effectiveness of the different potential vaccine components, a few specific components are then recommended to vaccine manufacturers and an entire, multibillion dollar process of manufacturing and distributing vaccines is initiated. Given the scale and critical health consequences of influenza vaccines, the results of the HI assays must be accurate and consistent. Therefore, the accuracy and consistency of the different readers across the various laboratories is also very important.

Methods and systems provided herein may, in an embodiment, determine an agglutination parameter in a reaction vessel potentially containing either a virus or a virus antibody. These systems and methods are versatile and may be used to determine a state of agglutination, non-agglutination, or non-specific inhibition and non-conforming agglutination results, such as an error state or condition. Further, the methods and systems provided herein are capable of detecting a wide range of hemagglutinin-containing viruses including adenoviruses, enteroviruses, flaviviruses, myxoviruses, poxviruses and reoviruses, including influenza hemagglutinin and influenza field isolates based on hemagglutinin inhibition. This is achieved, at least in part, by use of specially-constructed algorithms to automate vessel location and identification as well as vessel analysis to determine whether or not agglutination has occurred or, alternately, if the vessel indicates an error or non-specific inhibition.

Further provided is standardization across different laboratories by use of a specially configured quality control plate which compares and contrasts results by providing a fixed standard with an expected known outcome or agglutination parameter characterization. This can be an extremely useful and quick quality control check of device operating condition that reduces the subjectivity and variation inherent in generating agglutination parameters and titer values by utilizing expert human readers amongst different machines or within testing laboratories.

The systems and methods provided herein address a variety of problems associated with expert human readers, other attempts at automated agglutination readers and agglutination reactions in general. The need for expert human readers is avoided on every agglutination reaction or titer call while determining transition points between non-agglutination and agglutination reaction vessels. Further advantages include automated recognition or alerts of potential non-specific inhibition, and recognizing titer values outside of the dilution range provided in a reaction plate. The elimination of human readers not only reduces the error and subjectivity associated with any human determination, but also decreases operating costs and laboratory space required to perform agglutination reactions and titer determinations.

Also provided herein is the ability to record digital images for repeated analysis, with the digital images that may be later verified or confirmed by trained personnel as a second-check. Further provided are linked digital records of images, titer calls and associated sample and analysis information to reduce the risk of error during manual entry of data or loss of data due to tracking issues. The systems and methods can be used across the variety of hemagglutination (HA) and hemagglutination inhibition (HI) assay conditions including different types of cells or assay containers, such as U or V bottom microtiter plates. The methods and systems provided herein also provides the benefit of an increased consistency between different laboratories and, therefore, increases the compatibility of results in multi-laboratory projects, for example influenza vaccine selection.

Provided herein is optical imaging and digital recording of agglutination reactions with software-based analysis to determine an agglutination parameter, typically the relative titer (or concentration) of the agglutination reaction. Agglutination reactions are commonly used in medical diagnostics with samples of blood, urine, saliva, and cerebrospinal fluid. Agglutination has applications across a range of disciplines, including hematology (white and red blood cell typing), microbiology (viral and bacterial serotyping), and serology (detection of antibodies, such as in direct and indirect Coomb's test related to anemia, rheumatoid factor, and infectious diseases like syphilis, salmonella, Group B streptococcus, and many others). Hemagglutination (HA) and hemagglutination inhibition (HI) assays measure the titer of influenza virus and anti-influenza virus antibodies, respectively, and have been tested extensively. In an embodiment, the instrument scans and records the image of a 96-well microtiter plate containing agglutination reactions, and the software accepts user input such as dilution series and sample names. Image analysis follows a sequence of steps to locate the plate wells, analyze each well for the presence of agglutination, and assign titer values to individual samples. Images, input information, and titer calls are saved for later analysis and possible titer adjustment by the user. In addition to the instrument and software, a durable quality control plate has been developed that mimics an actual hemagglutination plate and helps standardize testing across different laboratories.

Up to this time, agglutination assays have predominately been read manually by trained experts, and significant variation has been noted between the titer determinations of different experts. For influenza hemagglutination assays, this lack of consistency or standardization between laboratories complicates the annual selection of influenza vaccines. In addition to the lack of standardization, expert human readers are expensive and limit the number of laboratories capable of performing the assays.

Other limitations associated with manual reading of agglutination assays involve the time sensitive nature of the assays and the complexity of tracking samples and associated titer values. Agglutination assays require that the plates be analyzed within 30 to 90 minutes after adding the final reagent. While an expert human reader can usually read a stack of plates quickly enough to support this requirement, interruptions can delay analysis until outside the recommended time window, rendering the result inaccurate. In addition, the timed reading window does not allow plates to be re-analyzed at some later date if concerns about accuracy or unusual results occur. Manual analysis also means manual recording of results, typically on paper, followed by transcription from the paper record to an electronic spreadsheet. The risk of misplaced records and transcription errors is significant, particularly when the agglutination assays are part of a high throughput operation with several thousand samples being processed per day.

The systems and methods contained herein provide several benefits by recording images and automating titer calls. Automated interpretation is a non-human means of consistently determining titer values independent of the laboratory and user. Titer values can therefore be standardized, and more laboratories will be able to perform and characterize agglutination assays with accurate results. By recording images and providing appropriate software, the methods and systems provided herein allows laboratories to operate in either real time or batch mode (serial image recording, followed by analysis later). Batch mode processing allows users to collect images and later approve titer calls without the time constraints of the agglutination assay. Digital image records and enabling software also allow titer calls to be re-evaluated at a later time to address new information and/or concerns with the previous analysis results.

Another benefit is the direct conversion from image to digital results without requiring manual notation and transfer. Conventional methods involving titer calls hand written on paper records or manually typed into spreadsheets introduce significant risk of errors. Accurate and comprehensive tracking from image and input data to titer calls in electronic records is more efficient than a manual process.

Another potential benefit is the detection of non-specific inhibition. Agglutination assays can be confounded by non-specific binding, where inhibition of the intended interactions are blocked by an interfering component in the sample. For example, HI assays measure the effect of anti-influenza antibodies binding to specific receptors on the influenza virus which then affects the ability of the virus to bind red blood cells and cause agglutination. The interactions between the antibodies, red blood cells, and virus are the intended interactions, but some samples can include other molecules that non-specifically bind to the antibodies, virus, and/or red blood cells and subsequently block or interfere with the desired antibody/virus/red blood cell interaction.

In general, non-specific inhibition in HI assay reaction wells affects the appearance of individual wells and can also cause the dilution series of a given sample to have unusual transitions from non-agglutinated to agglutinated. Expert human readers usually recognize the appearance and effects of non-specific inhibition, and make the appropriate decisions for titer calls and/or rejecting a given sample. Methods and systems provided herein are capable of distinguishing non-specific inhibition, while also providing the consistency and other advantages not present with human readers.

EXAMPLE 1

Hemagglutination Assay Protocol

A standard 10% solution of turkey red blood cells (RBC's) in Alsever's solution (Lampire Biologicals, CAT NO. 7209403) is prepared before performing the agglutination assay. After gently mixing, 4 mL turkey RBC's are pipetted into a 15 mL conical tube. The solution is centrifuged at 2500 RPM for 10 minutes, and the Alsever's solution is removed. After adding 12 mL of phosphate-buffered saline (PBS) to the packed cells and mixing gently, the solution is centrifuged at 2500 RPM for 5 minutes. The supernatant is removed, and the same PBS wash step is repeated twice more. Once the final wash is complete, the volume of packed cells is estimated and an appropriate volume of PBS added to obtain a 10% RBC suspension.

A working solution of 0.75% turkey RBC's hemagglutination plate assay is prepared by dispensing 1.875 mL of the 10.0% Turkey RBC solution into a 50 mL conical tube and adding 23.125 mL of 1×PBS to the 50 mL conical tube. The tube is then inverted multiple times to ensure the solution is homogenous.

A dilution series of influenza virus is prepared by thawing a sample of influenza A virus to room temperature and mixing the sample. Measured volumes of 1×PBS were dispensed into eight 1.5 mL tubes as described in the table below, and 160 μL of the virus stock solution is pipetted into the sample 1 tube. The solution in tube 1 is thoroughly mixed, and 480 μL is aspirated and dispensed into the sample 2 tube. The process of mixing and transferring 480 μL is repeated for the remaining tubes to create a dilution series of virus.

| Sample | Dilution created | Volume of virus added | Volume of PBS added |
|---|---|---|---|
| 1 | 1:6 | 160 μL (stock) | 800 μL |
| 2 | 1:12 | 480 μL (1:6) | 480 μL |
| 3 | 1:24 | 480 μL (1:12) | 480 μL |
| 4 | 1:48 | 480 μL (1:24) | 480 μL |
| 5 | 1:96 | 480 μL (1:48) | 480 μL |
| 6 | 1:192 | 480 μL (1:96) | 480 μL |
| 7 | 1:384 | 480 μL (1:192) | 480 μL |
| 8 | 1:768 | 480 μL (1:384) | 480 μL |

The 96-well plate is prepared by choosing a U bottom plate and dispensing 50 μL of 1×PBS into all wells in columns 2-12. 50 μL of the previously prepared virus sample 1 is placed into Well A1 of the plate. The 50 μL transfer is repeated for virus samples 2 through 8 in Wells B1 through H1, respectively (completing all rows in column 1). Similarly, 50 μL of virus samples 1 through 8 is placed in Wells A2 through H2 (column 2, all rows). Using a 200 μL multichannel pipette, all wells in Column 2 were mixed, and after mixing, 50 μL is transferred to Column 3. The process of mixing and 50 μL transfer is repeated for Columns 3 through 11 to create a 2-fold dilution series across the plate columns. 50 μL is aspirated and discarded from all wells in Column 11 to create an equal volume in all wells. Column 12 does not receive any virus sample and serves as a no-virus control.

In final form, the 96-well plate has a 2-fold virus dilution series both vertically and horizontally creating a gradient of virus concentration across and down the plate.

The red blood cells are added to the plate wells by placing the 0.75% turkey RBC solution into a trough matched to a 200 µL multichannel pipette. The multichannel pipette is used to mix the RBC solution with repeated aspirate & dispense cycles, and then 50 µL of the 0.75% turkey RBC solution is transferred into column 1 of the plate. The process of mixing and transfer is quickly repeated for all the plate columns. A timer is started after transferring to Column 12, and a clear adhesive film is applied over the plate. Plates with turkey red blood cells are analyzed (either manually, or using one of the software-based algorithm approaches described herein) approximately 30 minutes after adding RBC's.

EXAMPLE 2

Hemagglutination Inhibition Assay Protocol

Standard and working solutions of 10% and 0.75% turkey red blood cells (RBC's), respectively, are prepared following the same procedures as in Example 1.

A sample of influenza A virus is thawed to room temperature to prepare a working solution of virus at a dilution of 1:15. The 1:15 dilution is chosen because subsequent assay steps diluted the virus an additional 1:4, and a previous HA assay determined that a final dilution of 1:60 is approximately 4 times the minimum concentration necessary to cause agglutination with the 0.75% turkey RBC solution. To prepare the 1:15 virus solution, 2800 µL of PBS is dispensed into a 5 mL tube, the virus stock solution is mixed, and 200 µL of the virus stock solution is pipetted into the 5 mL tube. The 1:15 virus solution is thoroughly mixed.

Eight different samples of antisera are available. Antisera samples were previously treated with receptor destroying enzyme (RDE) to inactivate non-specific inhibitors, as well as being adsorbed with RBC's to remove non-specific agglutinins.

The 96-well plate is prepared by choosing a V bottom plate and dispensing 25 µL of 1×PBS into all wells in columns 2-12. 50 µL of antiserum 1 is dispensed into the Row A, Column 1 well, and the process of dispensing 50 µL of antiserum samples is repeated for samples 2 through 8 in Rows B through H, Column 1. A serial 1:2 dilution is performed across the plate from Column 1 to Column 11 by transferring 25 µL to the next column (from Column 1 to 2, etc.), mixing after each transfer, and finally discarding 25 µL from Column 11. No antiserum is applied to the wells in Column 12, as Column 12 is a non-agglutinated control column. 25 µL of the 1:15 virus solution is dispensed into all wells, and the wells mixed. The plate is covered and allowed to incubate for 15 minutes. 50 µL of the 0.75% turkey RBC solution is then added to all wells and mixed. The plate is covered, and allowed to incubate for 30 minutes. In final form, the 96-well plate had a 2-fold antiserum dilution series horizontally for each of the eight samples. A multichannel pipette is used, when appropriate, throughout the process.

EXAMPLE 3

Manual Reading of Hemagglutination Assay Plate

Figure 2:
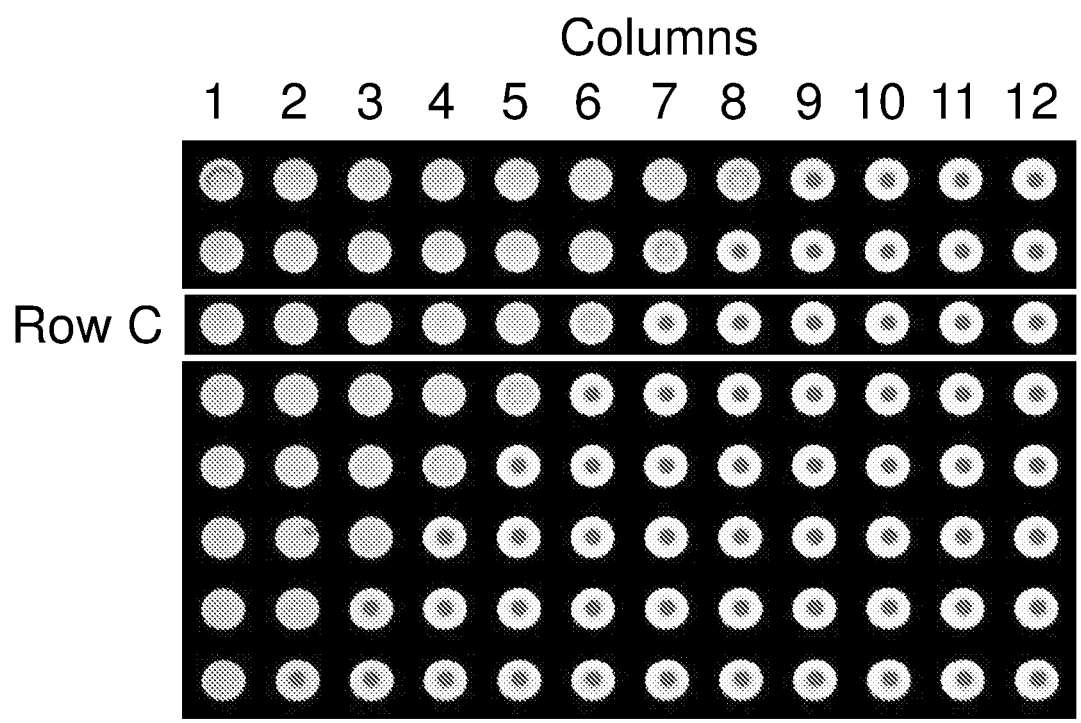
FIG. 2 is an image of an HA plate with Column 12 as non-agglutinated control wells.

In a well-lit laboratory space, 96-well microtiter plates with completed HA assays are viewed by an expert human reader. Reading is performed within minutes of the 30 minute incubation period ending. The human reader has a printed table listing each sample and a space to enter the assigned titer for each sample. The human reader also has a schematic plate layout illustrating the viral dilution factor for each column across the microtiter plate. The human reader reads each row of the plate following the same process of distinguishing agglutinated and non-agglutinated wells. For example, a reader reviewing Row C (third from the top) in FIG. 2 typically begins with the first well on the left and observes that the reaction is agglutinated due to its appearance as a uniform, slightly reddish solution across the well. The well in Row C, Column 2 has the same agglutinated appearance, and this pattern continued for Columns 3 through 5. The well in Column 6 appeared to have an approximately 3 mm diameter dot, or button, forming in the center of the well. This button is darker, i.e., greater optical density, than the surrounding matrix. The center button in the next well (Column 7) is clearly visible being darker and more obvious than in Column 6, and a close match to the non-agglutinated control well in Column 12. Columns 8 through 11 appeared essentially identical to Column 7. Column 6 is therefore chosen as the transition well from agglutinated to non-agglutinated, and the dilution factor associated with that well is assigned as the titer value. The human reader then writes the titer value for that first sample in the printed table. This process of viewing each row and determining the transition well and therefore the titer value is continued for all the samples in the plate.

Figure 3:
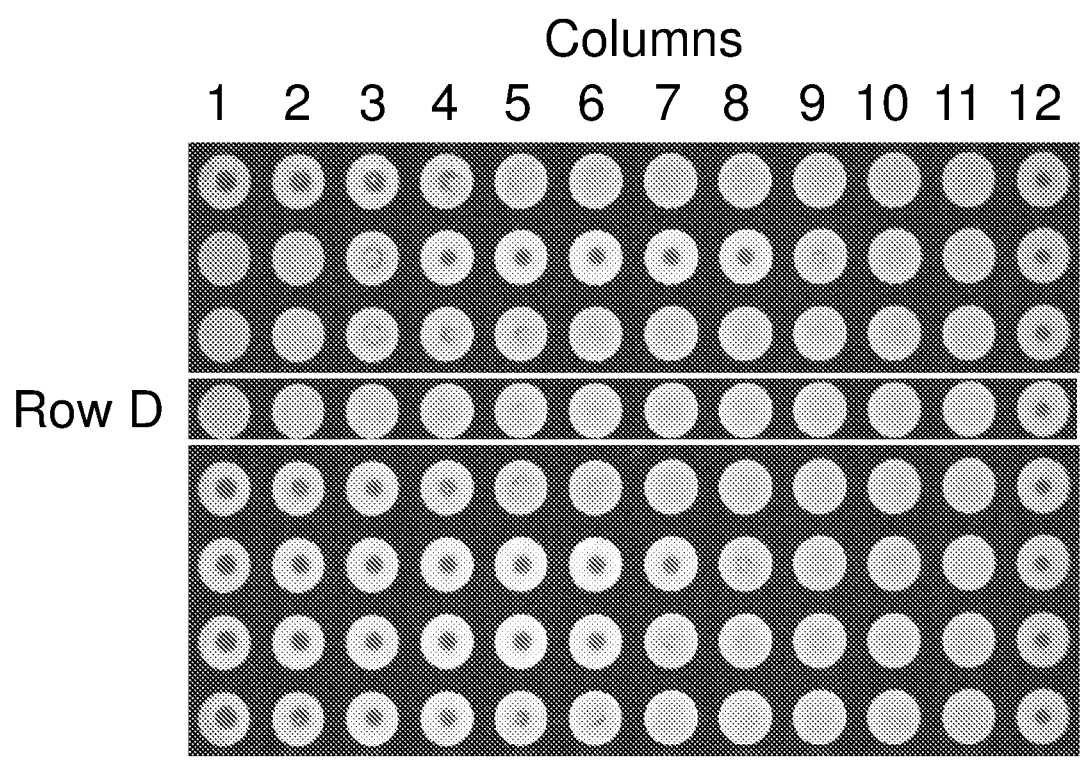
FIG. 3 is an image of an HI plate with Row D illustrating a row with only agglutinated reactions. Column 12 is non-agglutinated control wells.

In some cases, the manual reading process did not follow the standard steps described in the previous paragraph. If no transition well is observed across a row (columns 1 to 11), then a titer value is assigned that is either greater than or less than the most dilute and least dilute values, respectively. For example, FIG. 3 is a plate image where every well in Row D is agglutinated (Column 12 is the non-agglutinated control). The titer value for that row is assigned as ">10240" because the maximum dilution for that row is 10240. Conversely, if all the wells appeared non-agglutinated, then the titer value is assigned as "<the least concentrated dilution factor", i.e., "<10".

Figure 4:
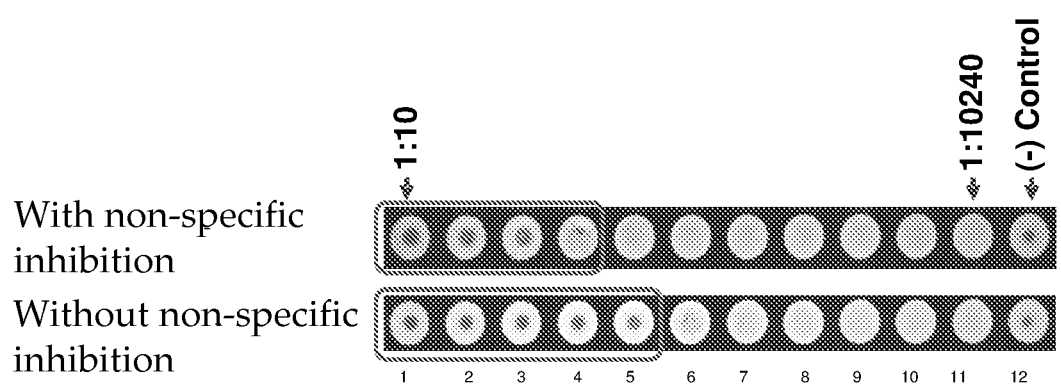
FIG. 4 is an image of two HI assays, with the top row illustrating a sample exhibiting non-specific inhibition, and the bottom row not exhibiting non-specific inhibition.

Another non-standard endpoint is identified when non-specific inhibition interferes with agglutination. Wells with strong non-specific inhibition appear as vague intermediate patterns between agglutinated and non-agglutinated with a center button that is larger than a non-agglutinated button and a diffuse wandering boundary. Non-specific inhibition occurs more frequently in HI assays, where the intended agglutination interactions between anti-virus antibodies, virus, and RBC's are complicated by the blocking effects of inhibitors on the antibodies, virus, and/or RBC's. An example image with non-specific inhibition is shown in FIG. 4. The wells in Column 1 to 3 of the top row illustrate the more diffuse and larger buttons associated with non-specific inhibition, compared to the control well (Column 12) and the standard HI assay wells in the bottom row. As the inhibitors are diluted out at lower concentrations (moving to the right in the plate image), the virus and RBC's do eventually agglutinate, but it is difficult to associate a sample dilution with the titer of the anti-virus antibody due to the presence of inhibitors. Inexperienced readers may assume that Column 4 of the top row is the transition well/titer value, but a more experienced expert would recognize the odd button appearance and highlight the presence of non-specific inhibition.

EXAMPLE 4

Receiver Plate and Vessel Location and Identification

An aspect of the instant methods and devices includes a receiver plate which both fixes a series of reaction vessels into known locations and blocks light transmission in areas not corresponding to reaction vessels. By fixing the location of the vessels or wells into repeatable, known positions, the algorithm for determining the position of the reaction vessels and therefore the areas to be analyzed within the digital image is simplified. Blocking transmission of light in areas not corresponding to reaction vessels simplifies both the well location and the step of analyzing the image for agglutination. The lack of light in areas not corresponding to vessels further eliminates forms of optical interference and increases the accuracy of the agglutination parameter determinations.

Imaging a fixed object like a 96-well plate and locating each well within the plate is necessary for automated titer determinations. While humans are generally exceptionally skilled at this type of visual pattern recognition, automated systems often struggle with the complexity of identifying a plate placed at various orientations and with features that vary depending on the manufacturer. When the added complexity of wells containing a range of optical densities and appearance is mixed in, automated methods to locate the plate and wells can be quite advanced and not necessarily compatible with an affordable, reliable laboratory instrument.

Figure 5:
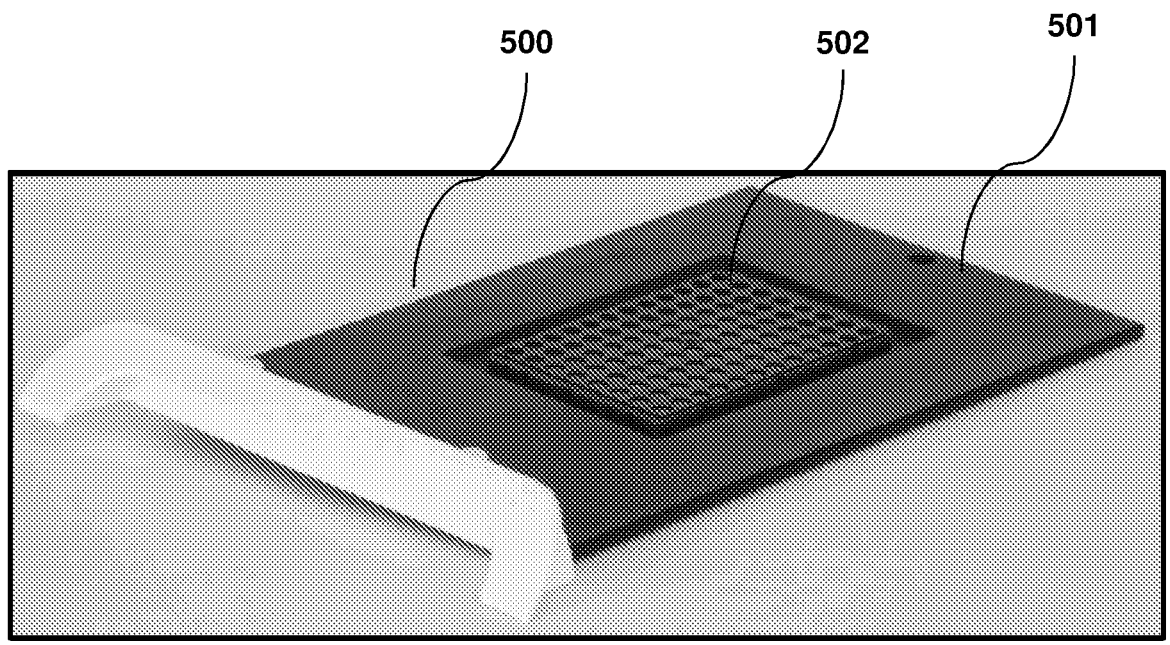
FIG. 5 illustrates a receiver plate for optically isolating reaction vessels, reducing optical scattering between vessels and positioning the reaction vessels in a repeatable location.
Figure 6:
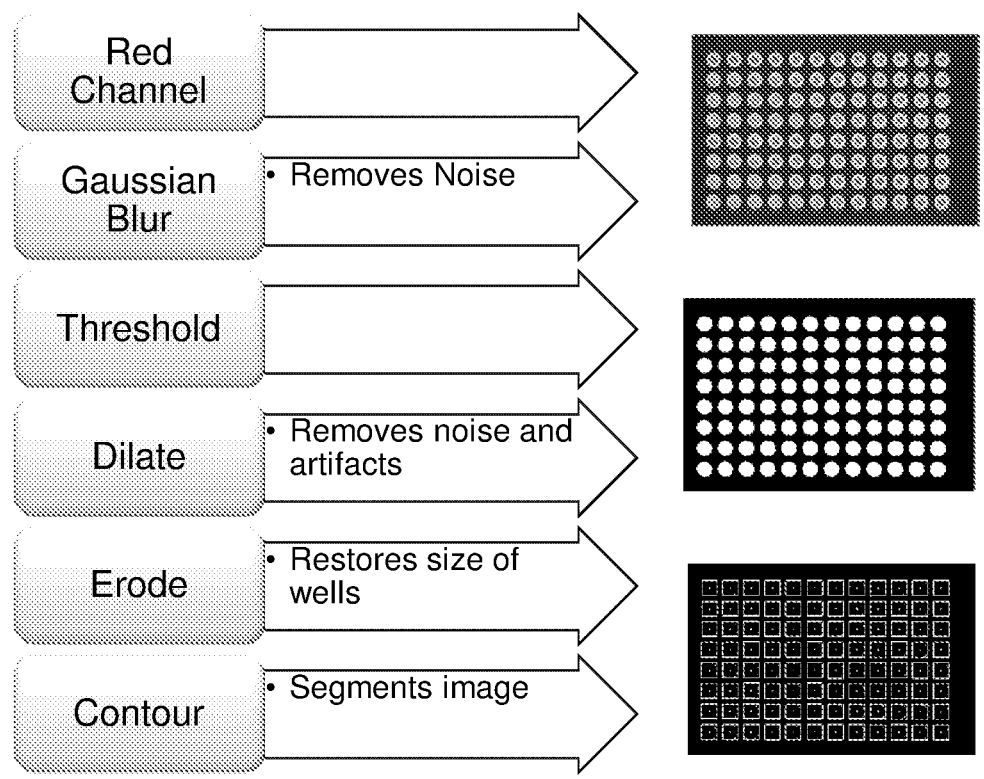
FIG. 6 is a flow chart and corresponding plate images of the process to locate and segment each well in a plate containing multiple reaction vessels.

Provided is an elegant combination of instrument hardware, electronics, and software to locate the plate and wells. First, a "receiver plate" is specifically configured to fit a given 96-well plate design and allow optical access to all 96 wells. This aspect is referred herein as the plated in optical communication with each other. Furthermore, this receiver plate aligns the 96-well plate with the optical imaging system and blocks optical scatter from other features like the walls and upper surface of the 96-well plate. FIG. 5 provides an example of a receiver plate 500 configured for 96 wells. The receiver plate has a surface 501 with a plurality of openings 502 to allow light to pass through the plate. Second, the well boundaries are accurately identified by a series of image analysis steps operating on the plate image recorded during scanning. FIG. 6 illustrates the sequence of analysis steps for determining vessel locations within the digital image containing a 96 well plate.

Figure 7:
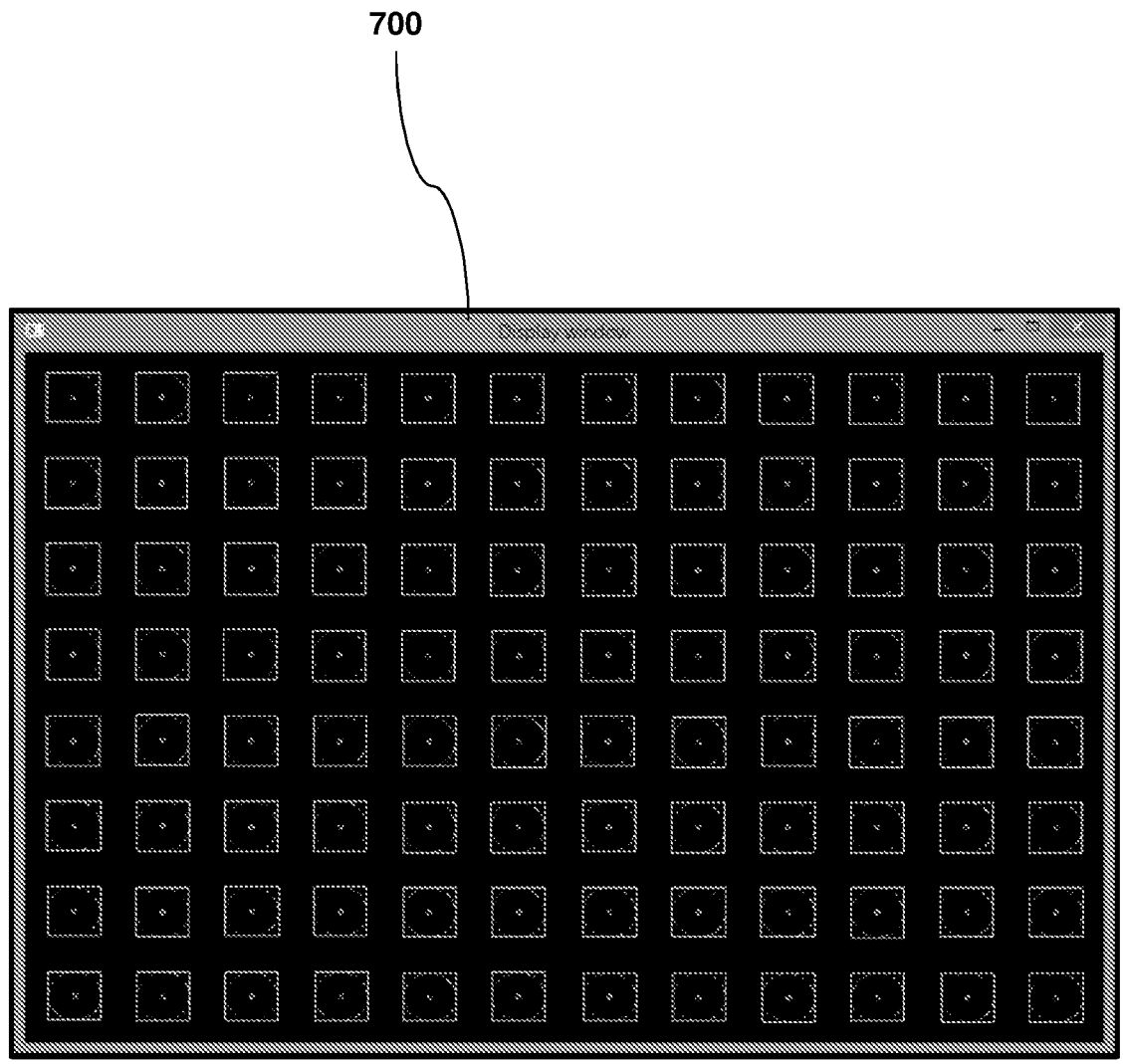
FIG. 7 illustrates a fully processed and segmented image of a well plate.

Well analyses may be performed by using output from all three detector channels (often referred to as RGB for red, green, and blue) in a "white light" analysis to identify plate and well locations. However, well locations are more reliably identified when only the red channel is analyzed in a digital image. In some cases, a large diameter non-agglutinated button can confound the plate and well algorithm when all three channels are used, or when the blue or green channels are used alone. However, the images from the red channel alone allow the wells to be accurately located First, the red channel image is blurred by a Gaussian function with a selected kernel size, such an 11×11 kernel size in a process known as Gaussian Blur or Gaussian smoothing to reduce image noise. The image is then put through a thresholding technique which distinguishes the visible areas from those shielded by the receiver plate. Thresholding converts the image to a binary image with the low intensity receiver tray areas of the image having signals of 0, or black, and the high transmission, high intensity wells having saturating, or white, signals. The image is then iteratively dilated to remove noise and artifacts. Next, the image is iteratively eroded to restore the original size of the wells or vessels. The dilate and erode processes involve a selected number of iterative cycles, such as ten iterative cycles each with a selected kernel size, such as 5×5 and a selected anchor point, such as 2,2. Finally, contour analysis segments the image into individual wells or vessels in which the agglutination reaction may occur, in this example into 96 separate images corresponding to each vessel within the 96-well plate. FIG. 7 illustrates a display 700 showing a fully processed image after segmentation, the square areas correspond to cropped images of the wells and the dots correspond to the automatically determined center of each well location. The automated identification process also reports an error if all 96 wells are not identified or their shapes and/or positions are substantially outside expected values.

EXAMPLE 5

Contour Analysis

Images corresponding to each individual reaction well or vessel are individually analyzed to determine the agglutination condition in each well. As previously explained, vessels or wells in which agglutination has taken place remain a generally uniform, transparent liquid whereas vessels in which agglutination has not taken place have a concentrated, optically opaque group of cells which have settled in the bottom of the well to form a "button".

Figure 8:
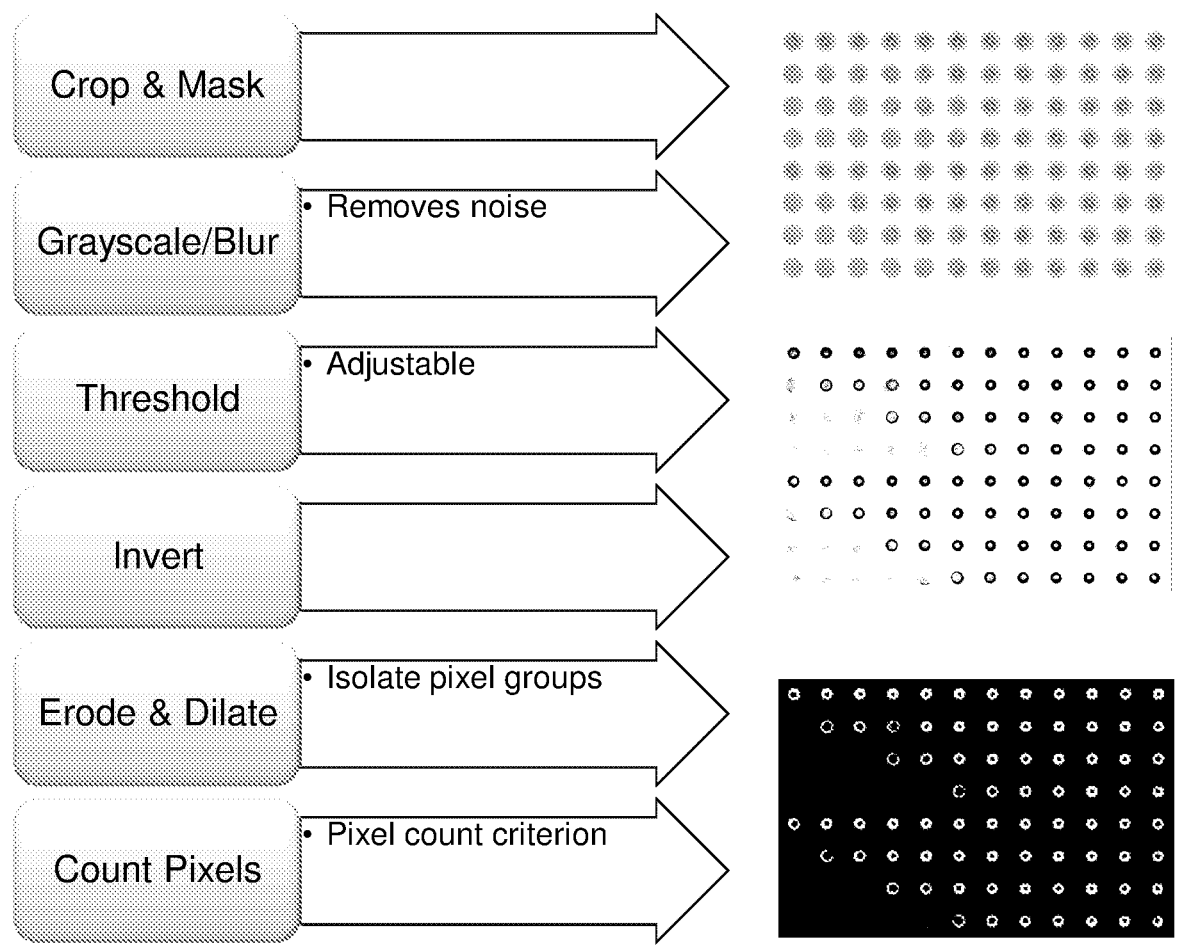
FIG. 8 is a flow chart and corresponding plate images of an analysis process to determine the agglutination parameter of a segmented image.

The segmented image in which the wells have been located and segmented undergoes several image processing steps, as illustrated in FIG. 8, that compare the non-agglutinated control wells with the sample wells. First, all well images are processed with a Gaussian blur (for example, kernel size: 3×3). Next, the signals of the blue and green detection channels are averaged to create a greyscale image of all wells. An adaptive threshold is then applied to convert the greyscale image to a black and white image (for example, method: adaptive Gaussian; threshold type: binary inversion; block size: 121; subtract constant: 3). A process of dilation and erosion using an elliptical structural element creates a low noise, smooth contour black and white image for all the wells. (for example, kernel size: 7×7; anchor Point: (−1,−1)). A contour finding algorithm is applied to identify the boundary in each well location.

After contours are identified in the preceding process steps, the contours within the control wells are analyzed to determine their respective centroid, radius, and circularity. Acceptable control wells have a centroid within a user-defined distance of the center of the well, such as a radius greater than 10% and less than 75% of the well radius, and the ratio of the minor and major axes of the best fit ellipse, i.e., circularity, must be within a user-defined range, such as within 70%, 80%, 90%, 95% or 99%. If more than one contour within the control well satisfies the criteria, then the feature with the largest radius is chosen as the control reference. If the control well does not have a contour that satisfies the criteria, then an error is reported. For control wells that satisfy the criteria, the contour is mapped, or overlaid, on the greyscale image, and the diameter and average intensity of the control button in the greyscale image are recorded for reference.

The parameters identified within the sample wells are then evaluated and compared to the control button parameters. Sample well parameters must have a centroid within a user-defined distance of the center of the well, and the ratio of the minor and major axes of the best fit ellipse, i.e., circularity, must be within a user-defined range. Sample wells that satisfy these criteria are then compared to the control button parameters of diameter and pixel intensity. The ratio of the sample button and the control button must be within a user-defined range, and similarly for the ratio of the sample and control button intensities, such as 80%, 90%, 95%, or, for example 99%. Sample wells with features that meet these criteria are determined to be non-agglutinated (like the controls), whereas sample wells with no contour-defined features or with features that do not meet the criteria are considered agglutinated.

After separating the sample wells into agglutinated and non-agglutinated, the transition well can be identified.

EXAMPLE 6

Quality Control Plate

Agglutination assays are difficult to standardize between different facilities or within the same facility at different times due to the variation in available reagents. For example, HA assays use a combination of red blood cells and virus. The age, biological source (avian, equine, guinea pig, human), and concentration of the red blood cells affect the agglutination and its appearance, and similar variables apply to the viral component of the assay. Hemagglutination inhibition assays add the additional biological variable of antibodies.

The lack of a standard assay or reference is an obstacle for automated analysis of agglutination reactions. Instruments in development, in production, or during installation at a user's site benefit from a consistent standard for characterizing performance. Comparing two instruments or the same instrument before and after transport to a user's site require that the plates being analyzed are essentially identical. The variability in agglutination assays makes creating nearly identical assay plates difficult, and the handling of biological materials makes instrument development impractical for engineers at facilities without wet lab capabilities. The lack of a consistent or idealized reference also complicates attempts to compare laboratories and verify uniform titer calls.

Figure 9:
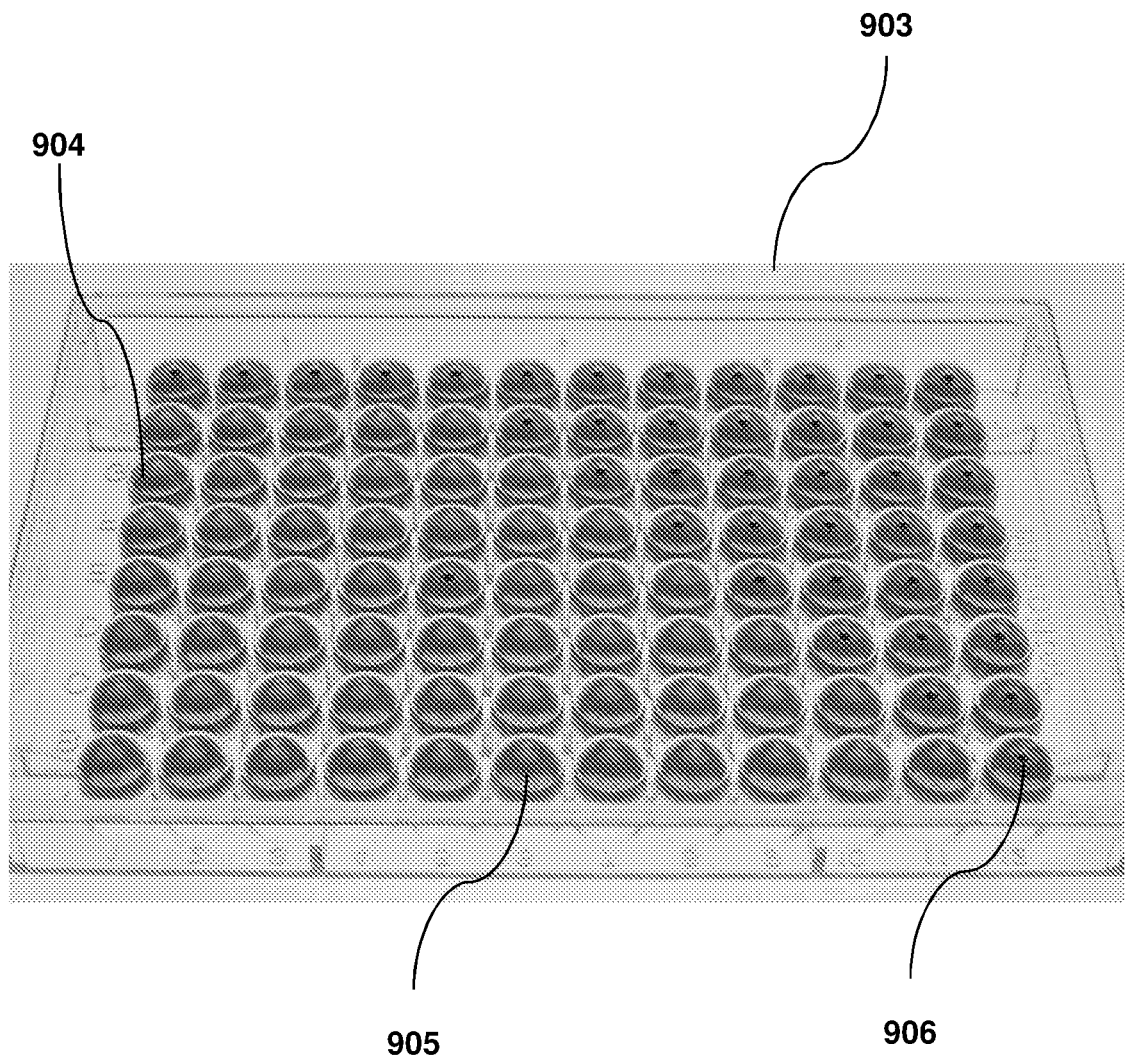
FIG. 9 is a fixed quality control plate which can be used to standardize analyzers and verify agglutination results (bottom view).
Figure 10:
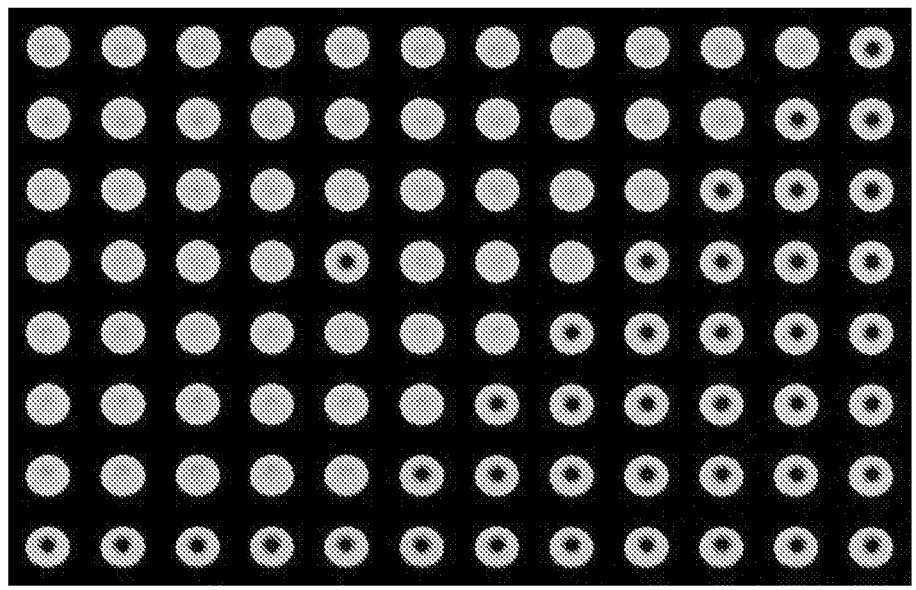
FIG. 10 is a comparison of images of the fixed quality control (QC) plate (top panel with an actual hemagglutination assay (HA) (bottom panel).
Figure 10:
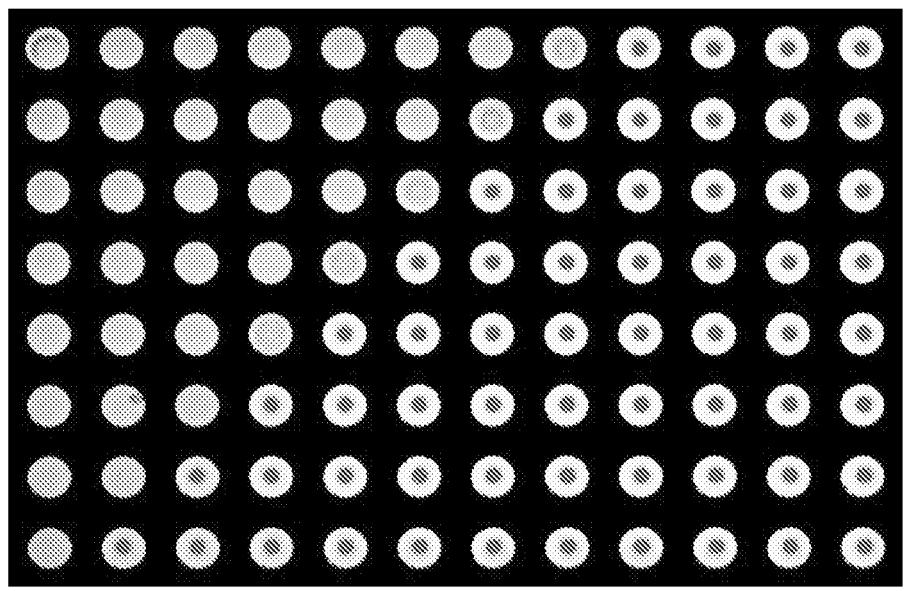

To address the need for a consistent agglutination reference, the systems and methods provided may include 96-well microtiter plates with wells that appear similar to HA and HI assay results, i.e., some wells with an optically dense button 906 at the bottom and center of the well, other wells with a uniform background across the well and no button and a background of reddish hue analogous to dilute blood, which may comprise a colored polymer 905. FIG. 9 shows an example of the quality control plate 903. The patterns within the wells 904 are permanent, or fixed, without spilling or shifting due to plate movement, and ambient storage conditions are sufficient to maintain the plate appearance (no refrigeration or humidity requirements). The pattern of wells with and without buttons can be varied and specified, and multiple replicates of the same plate appearance can be produced. The plates can be analyzed by the systems and methods provided herein or human readers to repeatedly create the same (simulated) titer determinations. FIG. 10 illustrates an image comparison of the quality control plate (top panel) and an actual hemagglutination assay (bottom panel).

Quality Control plates may be produced by preparing an epoxy solution with an optical pigment, such as 0.05% red pigment (by volume) (Smooth-On EpoxACast 690; Real Milk Paint Pigment (red)). A volume of the pigmented epoxy solution is dispensed into each well of the U or V bottom 96-well plate, such as a 100 µL volume. Non-agglutinated wells are simulated by adding a solid element that provides optical contrast, such as a 1/16" diameter ball bearing to the well. Lids are placed on the plates, and the plates are stored for a minimum of 24 hours to cure the epoxy before use and packaging.

EXAMPLE 7

Device and User Interface

Figure 11:
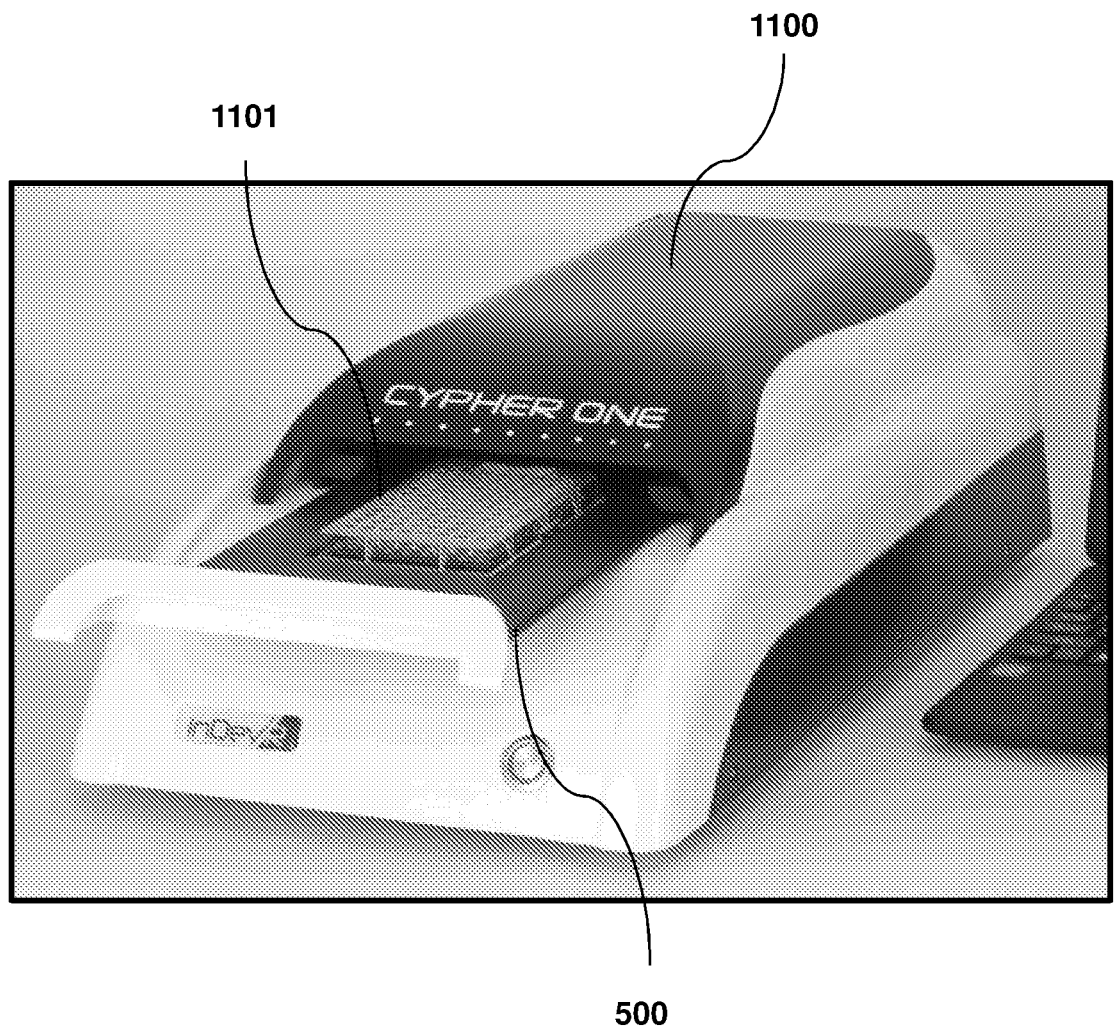
FIG. 11 illustrates a standalone device with the receiver plate positioning a 96 well reaction plate.

The systems and methods can be utilized by an integrated device and software package to fully automate the determination of agglutination parameters or several agglutination parameters to establish a titer call. In the present example, the device is a standalone unit containing the receiver plate in a 96 well configuration and a digital imaging device. FIG. 11 illustrates the standalone analyzer 110 with a reaction plate 1101 with 96 wells loaded into the receiver plate 500. Within the analyzer 1100 are is an optical source and an optical detector. In some embodiments, the analyzer may further comprise a processor or may be in electronic communication with an external processor. The standalone device itself may perform the analysis described herein, or may be placed in electronic communication with a standard desktop, laptop computer, or other electronic computing device to performs the analysis described herein.

Figure 12:
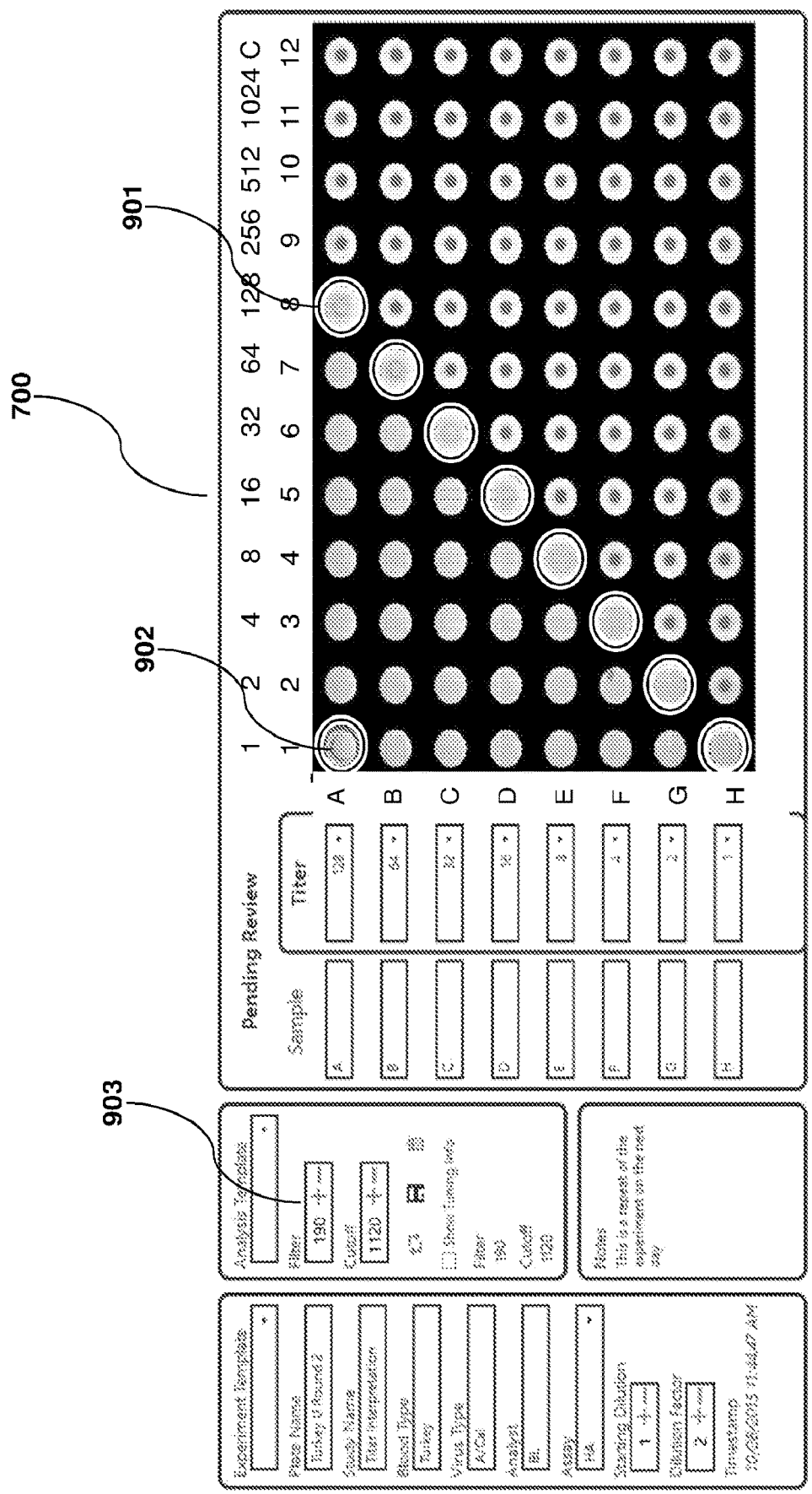
FIG. 12 is a graphical user interface showing determined transition points, potential errors and adjustable parameters, along with an optical image of the reaction plate.

The user interface, whether contained in an inclusive device or a separate computer device, provides advantages over similar attempts to automate the agglutination process. Rather than converting data into resulting agglutination parameters or chart representations, the digital image may be stored for later reinterpretation by expert human readers or by altering the automated analysis parameters to refine results or remove errors. Additionally, because the user interface includes the image of the reaction plates, non-specific inhibition or imaging errors may be easily identified both by the human user or the analysis programming, either in real time or later review. FIG. 12 illustrates one example of a user interface on a display 700. Also highlighted is the transition from agglutinated to non-agglutinated vessels 901 for the user to verify visually, in this case as a diagonal line moving downwards from left to right. Methods and systems may also be provided to identify images of vessels in which it is determined there is a problem or potential error 902. This allows the user to quickly identify whether an imaging error may have occurred. Additionally, because the images are stored they may later be reviewed if not scrutinized in real time to determine if errors or non-specific inhibition led to an inaccurate agglutination parameter or determined titer value.

The automated analysis parameters 903 may be adjusted with the results in view, to ensure the automated results are calibrated and align with the expected visual interpretation. This allows for simple and reliable calibration and verification by expert readers. Again, since the digital images are stored they may also be reviewed and adjusted later to refine results without the need to perform the agglutination reactions for a second time.

EXAMPLE 8

Performance of Device

The systems and methods can be utilized to fully automate the determination of the agglutinated state of the experimental sample to determine a titer call. In the present example, hemagglutination inhibition assays were completed to yield 1,241 individual sample analyses from seven unique experimental groups.

Samples were first analyzed using the system and algorithm of the current invention. Both the filter and cutoff were optimized for each experimental group.

During the analysis, the expert human reader utilized a method involving plate tilting to help distinguish non-specific inhibition. This method consisted of tilting the plate within a fixture, set at a 45 degree angle, for approximately 30 seconds or until the movement of the "button" was acceptable. The plate was then transferred to secondary flat fixture, including a 45 degree mirror underneath the plate, which was used to aid in the visualization for the expert human reader. Upon interpretation, the expert human reader would record the titer values for each sample on a sheet of paper. This record would then be transcribed to an electronic record.

The direct comparison between the systems interpretation herein and that of the expert human reader for all 1,241 samples resulted in 94.5% agreement within (+/− 1 dilution).

STATEMENTS REGARDING INCORPORATION BY REFERENCE AND VARIATIONS

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

All patents and publications mentioned in the specification are indicative of the levels of skill of those skilled in the art to which the invention pertains. References cited herein are incorporated by reference herein in their entirety to indicate the state of the art, in some cases as of their filing date, and it is intended that this information can be employed herein, if needed, to exclude (for example, to disclaim) specific embodiments that are in the prior art. For example, when a compound is claimed, it should be understood that compounds known in the prior art, including certain compounds disclosed in the references disclosed herein (particularly in referenced patent documents), are not intended to be included in the claim.

When a group of substituents is disclosed herein, it is understood that all individual members of that group and all subgroups, are disclosed separately. When a Markush group or other grouping is used herein, all individual members of the group and all combinations and subcombinations possible of the group are intended to be individually included in the disclosure. Specific names of compounds are intended to be exemplary, as it is known that one of ordinary skill in the art can name the same compounds differently.

It must be noted that as used herein and in the appended claims, the singular forms "a", "an", and "the" include plural reference unless the context clearly dictates otherwise. Thus, for example, reference to "an agglutinating mediator" includes a plurality of such mediators and equivalents thereof known to those skilled in the art, and so forth. As well, the terms "a" (or "an"), "one or more" and "at least one" can be used interchangeably herein. It is also to be noted that the terms "comprising", "including", and "having" can be used interchangeably. The expression "of any of claims XX-YY" (wherein XX and YY refer to claim numbers) is intended to provide a multiple dependent claim in the alternative form, and in some embodiments is interchangeable with the expression "as in any one of claims XX-YY."

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. Nothing herein is to be construed as an admission that the invention is not entitled to antedate such disclosure by virtue of prior invention.

Every formulation or combination of components described or exemplified can be used to practice the invention, unless otherwise stated. Specific names of materials are intended to be exemplary, as it is known that one of ordinary skill in the art can name the same material differently. One of ordinary skill in the art will appreciate that methods, device elements, starting materials, and synthetic methods other than those specifically exemplified can be employed in the practice of the invention without resort to undue experimentation. All art-known functional equivalents, of any such methods, device elements, starting materials, and synthetic methods are intended to be included in this invention.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. Any recitation herein of the term "comprising", particularly in a description of components of a composition or in a description of elements of a device, is understood to encompass those compositions and methods consisting essentially of and consisting of the recited components or elements. In each instance herein any of the terms "comprising", "consisting essentially of" and "consisting of" may be replaced with either of the other two terms. The invention illustratively described herein suitably may be practiced in the absence of any element or elements, limitation or limitations which is not specifically disclosed herein.

Whenever a range is given in the specification, for example, a temperature range, a time range, or a composition or concentration range, all intermediate ranges and subranges, as well as all individual values included in the ranges given are intended to be included in the disclosure. As used herein, ranges specifically include the values provided as endpoint values of the range. For example, a range of 1 to 100 specifically includes the end point values of 1 and 100. It will be understood that any subranges or individual values in a range or subrange that are included in the description herein can be excluded from the claims herein.

One of ordinary skill in the art will appreciate that starting materials, biological materials, reagents, synthetic methods, purification methods, analytical methods, assay methods, and biological methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, exemplary embodiments and optional features, modification and variation of the concepts herein disclosed may be resorted to by those skilled in the art, and that such modifications and variations are considered to be within the scope of this invention as defined by the appended claims. The specific embodiments provided herein are examples of useful embodiments of the present invention and it will be apparent to one skilled in the art that the present invention may be carried out using a large number of variations of the devices, device components, methods steps set forth in the present description. As will be obvious to one of skill in the art, methods and devices useful for the present methods can include a large number of optional composition and processing elements and steps.

We claim:

1. A method for determining an agglutination parameter with particles in a fluid sample, said method comprising the steps of:
    providing a reaction plate having a plurality of reaction vessels;
    introducing an agglutinating mediator to at least a portion of said plurality of reaction vessels, wherein said introduced agglutinating mediator in said reaction vessels spans a dilution range over said at least a portion of said plurality of reaction vessels;
    introducing said particles in the fluid sample to each of said plurality of reaction vessels,
    creating a digital image of said plurality of reaction vessels;
    processing said digital image to generate a processed image, wherein said step of processing comprises defining a plurality of areas of said processed image corresponding to each of said plurality of reaction vessels and each of said areas correspond to a plurality of pixels;
    measuring within each of said defined plurality of areas a pixel intensity for each of said plurality of pixels positioned within said area;
    identifying a boundary contour, if present, for each of said reaction vessels from said measuring step;
    calculating a one or more boundary contour parameters for each of said identified boundary contours;
    comparing each of said calculated one or more boundary contour parameters in each of said reaction vessels with a one or more standard boundary contour parameters from a control reaction vessel having a non-agglutination control or an agglutination control to determine an agglutination condition in each of said plurality of reaction vessels, wherein said agglutination condition is one of: agglutination, non-agglutination, non-specific inhibition, or error state; and
    determining said agglutination parameter from said agglutination condition that is agglutination or non-agglutination in at least a portion of said plurality of reaction vessels over said dilution range, wherein said agglutination parameter is titer or concentration of said agglutination mediator.

2. The method of claim 1, wherein said one or more standard boundary contour parameters is a user-provided value.

3. The method of claim 1, wherein said reaction plate further comprises a control reaction vessel and the method further comprises the steps of:
    introducing a control fluid sample into said control reaction vessel, wherein said control fluid sample non-agglutinates and forms a central button in a central region of said control reaction vessel;
    creating a digital image of said control reaction vessel;
    processing said digital image to generate a processed image, wherein said step of processing comprises defining a control area of said processed image corresponding to said control reaction vessel and said control area corresponds to a plurality of pixels;
    measuring within said defined control area a pixel intensity for each of said plurality of pixels positioned within said area;
    identifying a standard non-agglutination boundary contour with a one or more standard boundary contour parameter for said control fluid sample in said control reaction vessel, from said measuring step.

4. The method of claim 3, wherein said control reaction vessel comprises at least two control reaction vessels, wherein:
    a first control reaction vessel is a positive control reaction vessel where agglutination occurs so that no button is optically detected to provide a first standard boundary contour parameter having said agglutination control; and
    a second control reaction vessel is a negative control reaction vessel where non-agglutination occurs and a centrally-positioned button is optically detected to provide a second standard boundary contour parameter having said non-agglutination control.

5. The method of claim 3, wherein said step of introducing the control fluid sample into said control reaction vessel is performed in a control reaction plate that is different than said reaction plate of said providing step.

6. The method of claim 1, wherein said identifying said boundary contour step comprises edge detection.

7. The method of claim 6, wherein said edge detection comprises identifying a pixel intensity gradient that is greater than or equal to a pixel intensity gradient of the non-agglutination control.

8. The method of claim 1, wherein said boundary contour parameters are selected from the group consisting of:
    an area defined by said boundary contour;
    a perimeter of said boundary contour;
    a circularity of said boundary contour;
    an optical intensity of a region confined by said boundary contour;
    an average pixel gradient intensity of said boundary contour;

a ratio of average pixel intensity of a region within said boundary contour to average pixel intensity in a region outside said boundary contour;

a location of said boundary contour within said area;

a diameter of an area defined by said boundary contour;

a pixel intensity density within said reaction vessel; and any combination thereof.

9. The method of claim 1, wherein said non-specific inhibition is identified in a reaction vessel having a non-uniform boundary contour, multiple boundary contours, or boundary contour diameter exceeding a well contour diameter of said non-agglutination control.

10. The method of claim 1, further comprising the step of identifying said error state in at least one said control reaction vessel without an identifiable boundary contour.

11. The method of claim 1, wherein said boundary contour parameters are one or more of area of a region defined by said boundary contour, circularity, or location of said boundary contour within the reaction vessel.

12. The method of claim 1, further comprising the step of automatically optically detecting a position of said control reaction vessel.

13. The method of claim 1, wherein said agglutinating mediator is selected from the group consisting of: a virus, an antibody, a complement, a vaccine, and a combination thereof.

14. The method of claim 1, wherein said particles are red blood cells, and said agglutinating mediator is a virus.

15. The method of claim 14, wherein said agglutinating mediator further comprises a vaccine or component thereof, and said agglutination parameter is a titer of said vaccine or component thereof.

16. The method of claim 1, further comprising the step of:
positioning said reaction plate in a receiver plate, wherein said receiver plate has a plurality of openings aligned with said plurality of reaction vessels to optically isolate said areas corresponding to said plurality of reaction vessels to increase an optical contrast between a well boundary of each of said reaction vessels and a fluid sample receiving volume formed by said well boundary.

17. The method of claim 1, wherein said step of processing said digital image further comprises the step of isolating a red channel of said digital image to define said area of said processed image corresponding to each of said reaction vessels.

18. The method of claim 1, wherein said step of processing said digital image further comprises converting said digital image to greyscale.

19. The method of claim 1, wherein said step of processing said digital image further comprises dilating and eroding said digital image by applying a rectangular structural element.

20. The method of claim 1, wherein said step of processing said digital image further comprises performing a Gaussian blur of said digital image.

21. The method of claim 1, wherein said step of processing said digital image further comprises separating said digital image into a red channel, a blue channel and a green channel.

22. The method of claim 1 further comprising the step of:
providing a quality control plate and repeating said creating, processing, measuring, identifying, calculating, comparing and determining steps on said quality control plate;

comparing the determined agglutination parameter for said quality control plate against a known agglutination parameter for said quality control plate;

thereby obtaining an instrument verification parameter from said quality control plate.

23. The method of claim 22, wherein said quality control plate comprises a plurality of vessels with optically dense buttons and a plurality of vessels without optically dense buttons and the method further comprises standardizing the method across different automated agglutination analyzers that implement said method.

24. The method of claim 22, wherein said quality control plate contains no liquid.

25. The method of claim 24, wherein said reaction plate and quality control plate are each a 96-well plate, and each of said quality control plate reaction vessels are filled with a colored polymer and said reaction vessels having optically dense buttons corresponding to a solid centrally-positioned within the reaction vessel and embedded in the polymer.

26. The method of claim 1, wherein said agglutination mediator comprises an influenza virus or anti-influenza virus antibodies.

27. A method for determining validation status of an automated agglutination analyzer, the method comprising the steps of:

providing a quality control plate to a reservoir plate of the analyzer, wherein the quality control plate has a plurality of wells, including a first set of wells having an optically dense button and a second set of wells without the optically dense button;

creating a digital image of said plurality of wells;

processing said digital image to generate a processed image, wherein said step of processing comprises defining a plurality of areas of said processed image corresponding to each of said plurality of wells;

measuring within each of said defined plurality of areas a pixel intensity for each of said plurality of pixels positioned within said area;

identifying a boundary contour, if present, for each of said plurality of wells from said measuring step;

calculating a one or more boundary contour parameters for each of said identified boundary contours; and comparing each of said calculated one or more boundary contour parameters in each of said reaction vessels with a one or more standard boundary contour parameters corresponding to non-agglutination or agglutination, thereby determining validation status of said automated agglutination analyzer, wherein:

for the comparing step that results in each of said plurality of wells corresponding to non-agglutination for the wells having the optically dense button or agglutination for the wells having the not optically dense button the automated agglutination analyzer is validated; or the comparing step that results in at least one of said reaction vessels that is not non-agglutination for wells having the optically dense button and that is not agglutination for the wells not having the optically dense button, the automated agglutination analyzer is not validated.

* * * * *